United States Patent
Hei et al.

(10) Patent No.: US 6,534,075 B1
(45) Date of Patent: Mar. 18, 2003

(54) ANTIMICROBIAL AND ANTIVIRAL COMPOSITIONS AND TREATMENTS FOR FOOD SURFACES

(75) Inventors: Robert D. P. Hei, Baldwin, WI (US); Kim R. Smith, Woodbury, MN (US); Polly D. Laugen, Minnetonka, MN (US); Bruce R. Cords, Eagan, MN (US); Shaun P. Kennedy, North Oaks, MN (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 09/277,626

(22) Filed: Mar. 26, 1999

(51) Int. Cl.⁷ .................. A01N 33/12; A01N 59/00; A23B 4/20; A23B 5/14; A23L 3/3526
(52) U.S. Cl. .................. 424/405; 134/25.2; 134/25.3; 210/753; 210/754; 210/755; 210/756; 422/32; 422/37; 424/43; 424/616; 424/632; 424/661; 424/663; 424/665; 424/667; 424/669; 424/670; 424/671; 424/723; 426/66; 426/318; 426/326; 426/332; 426/335; 426/532; 514/2; 514/561; 514/642; 510/111; 510/218; 510/234; 510/367; 510/370; 510/371; 510/372; 510/373; 510/376; 510/379; 510/380; 510/384; 510/385; 510/391
(58) Field of Search .................. 425/66, 318, 320, 425/323, 326, 332, 335, 532; 424/43, 44, 45, 46, 47, 405, 410, 415, 613, 616, 632, 661, 662, 663, 664, 665, 667, 668, 669, 670, 671, 672, 723, 76.21, 76.8, 76.9; 422/28, 32, 37, 29; 210/753, 754, 755, 756, 759; 134/25.2, 25.3; 514/2, 21, 562, 642; 510/111, 133, 218, 219, 234, 304, 319, 367, 370, 371, 372, 373, 375, 376, 379, 380, 382, 383, 384, 385, 391, 490, 504, 131, 132, 137, 237

(56) References Cited

U.S. PATENT DOCUMENTS

| | | | |
|---|---|---|---|
| 2,193,636 A | * 3/1940 | Marshall | 426/323 |
| 2,512,640 A | 6/1950 | Greenspan et al. | 514/557 |
| 2,662,855 A | 12/1953 | Kamlet | 504/119 |
| 2,666,010 A | 1/1954 | Stayner | 514/642 |
| 2,679,533 A | 5/1954 | Darragh et al. | 564/282 |
| 2,692,231 A | 10/1954 | Stayner et al. | 504/158 |
| 2,740,744 A | 4/1956 | Abramitis et al. | 514/642 |
| 2,746,928 A | 5/1956 | Darragh et al. | 510/384 |
| 2,751,713 A | 6/1956 | Abramitis | 504/101 |
| 2,863,798 A | 12/1958 | Shelanski et al. | 424/672 |
| 2,868,686 A | 1/1959 | Shelanski et al. | 424/672 |
| 2,917,428 A | 12/1959 | Hitzman | 424/616 |
| 3,152,073 A | 10/1964 | Morton | 514/642 |
| 3,194,758 A | 7/1965 | Lissant | 210/732 |
| 3,223,643 A | 12/1965 | Law | 510/384 |
| 3,344,018 A | 9/1967 | Shibe, Jr. et al. | 514/231.2 |
| 3,380,923 A | 4/1968 | Beach | 510/385 |
| 3,525,696 A | 8/1970 | Schmidt et al. | 510/234 |
| 3,749,673 A | 7/1973 | Jones et al. | 8/108.1 |
| 3,778,476 A | 12/1973 | Rembaum et al. | 525/539 |
| 3,898,336 A | 8/1975 | Rembaum et al. | 424/447 |

(List continued on next page.)

FOREIGN PATENT DOCUMENTS

| | | |
|---|---|---|
| DE | 18 13 584 | 10/1969 |
| DE | 28 21 199 | 11/1978 |
| DE | 29 05 373 | 9/1979 |
| DE | 41 37 544 A1 | 5/1993 |
| EP | 0 086 423 | 8/1983 |
| EP | 0 087 049 A1 | 8/1983 |
| EP | 0 095 377 A1 | 11/1983 |
| EP | 0 156 646 | 10/1985 |
| EP | 0 185 970 A1 | 7/1986 |
| EP | 0 214 850 A2 | 3/1987 |
| EP | 0 443 640 | 8/1991 |
| EP | 0 832 964 A1 | 4/1998 |
| EP | 1 001 012 A1 | 5/2000 |
| FR | 2663852 * | 1/1992 |
| GB | 898820 | 6/1962 |
| GB | 1 265 919 | 3/1972 |
| GB | 1 301 861 | 1/1973 |
| GB | 1346594 | 2/1974 |
| GB | 2132087 A | 7/1984 |
| GB | 2 268 879 | 1/1994 |
| JP | 4-82959 | 3/1992 |
| JP | 4-107223 | 4/1992 |

(List continued on next page.)

OTHER PUBLICATIONS

U.S. Provisional Application 60/056,622, Aug. 20, 1997.*
Roberts et al. Bask Principles Of Organic Chemistry, 2nd ed. Menlo Park: W.A. Benjamin, Inc. pp. 1176, 1328, 1977.*
Abdelkader, M. et al. Spectrophotometric Analysis of Quaternized Drugs, *Pharmazie*, vol. 35, pp. 30–32 (1980).
Arm. Khim. Zh., vol. 38, No. 1, pp. 53–57 (1985).
Baleux, M. et al., "Physicochimie Collaidale," *C. R. Acad. Sc. Paris*, pp. 11–35–1138 (1966).
"Chemical Abstracts", *The American Chemical Society*, vol. 121, No. 15, (Oct. 10, 1994), pp. 546–547.
Chowdhury, A.N. et al., "Improved Rapid Determination of Nickel in Soils and Laterites," *Analytical Chemistry*, pp. 820–821 (Jun. 1960).

Primary Examiner—Jeffrey E. Russel
(74) Attorney, Agent, or Firm—Merchant & Gould P.C.

(57) ABSTRACT

An antimicrobial and antiviral composition in powder form or in the form of a two part liquid concentrate for washing and sanitizing foods, food surfaces, food ware, process waters, animal quarters, and animal carcasses is described. The composition may also be used to reduce the microbial and viral population on animals; reducing human pathogenic microbes, reducing opportunistic pathogenic microbes on eggs, and treating skin diseases. The composition includes three reactive species which in solution form an oxidizing species, and optionally a food grade acid source. The reactive species include a natural source of a quaternary or protonizable nitrogen compound which is acceptable on foods, an oxidant and a halide source.

66 Claims, No Drawings

U.S. PATENT DOCUMENTS

| | | | | |
|---|---|---|---|---|
| 3,958,020 A | * | 5/1976 | DeVries | 426/265 |
| 3,966,090 A | * | 6/1976 | Prussin et al. | 222/94 |
| 4,051,058 A | | 9/1977 | Bowing et al. | 424/616 |
| 4,051,059 A | | 9/1977 | Bowing et al. | 252/186.23 |
| 4,073,888 A | | 2/1978 | Snyder | 424/661 |
| 4,111,679 A | | 9/1978 | Shair et al. | 504/160 |
| 4,113,857 A | | 9/1978 | Shetty | 424/78.25 |
| 4,206,233 A | | 6/1980 | Quinlan | 514/642 |
| 4,336,152 A | | 6/1982 | Like et al. | 510/106 |
| 4,397,757 A | | 8/1983 | Bright et al. | 252/186.41 |
| 4,592,488 A | | 6/1986 | Simon et al. | 222/94 |
| 4,597,975 A | | 7/1986 | Woodward et al. | 514/644 |
| 4,654,208 A | | 3/1987 | Stockel et al. | 514/252 |
| 4,737,307 A | | 4/1988 | Brown et al. | 252/106 |
| 4,741,851 A | | 5/1988 | Borrello | 252/91 |
| 4,822,513 A | | 4/1989 | Corby | 252/106 |
| 4,824,867 A | | 4/1989 | Smith et al. | 514/642 |
| 4,857,223 A | | 8/1989 | Borrello | 252/91 |
| 4,874,788 A | | 10/1989 | Smith et al. | 514/534 |
| 4,900,721 A | | 2/1990 | Bansemir et al. | 514/25 |
| 4,937,072 A | | 6/1990 | Kessler et al. | 424/94.4 |
| 4,941,989 A | | 7/1990 | Kramer et al. | 252/102 |
| 4,960,590 A | | 10/1990 | Hollis et al. | 424/78 |
| 4,976,874 A | | 12/1990 | Gannon et al. | 210/755 |
| 5,047,164 A | | 9/1991 | Corby | 252/106 |
| 5,070,105 A | | 12/1991 | Segall et al. | 514/626 |
| 5,081,106 A | | 1/1992 | Bentley et al. | 514/5 |
| 5,093,078 A | | 3/1992 | Hollis et al. | 422/16 |
| 5,117,049 A | | 5/1992 | Venturello et al. | 562/2 |
| 5,200,189 A | | 4/1993 | Oakes et al. | 424/405 |
| 5,202,047 A | | 4/1993 | Corby | 252/106 |
| 5,264,191 A | | 11/1993 | Nakao et al. | 423/22 |
| 5,320,805 A | | 6/1994 | Kramer et al. | 422/28 |
| 5,366,983 A | | 11/1994 | Lattin et al. | 514/358 |
| 5,545,349 A | * | 8/1996 | Kurii et al. | 252/186.38 |
| 5,620,527 A | | 4/1997 | Kramer et al. | 134/2 |
| 5,658,467 A | | 8/1997 | LaZonby et al. | 210/754 |
| 5,683,724 A | | 11/1997 | Hei et al. | 424/616 |
| 5,756,090 A | * | 5/1998 | Allen | 424/94.4 |
| 6,106,854 A | * | 8/2000 | Belfer et al. | 424/405 |
| 6,165,485 A | * | 12/2000 | Alther | 424/421 |
| 6,251,386 B1 | * | 6/2001 | Johansen | 424/94.4 |
| 2001/0009664 A1 | * | 7/2001 | Johansen | 424/94.4 |

FOREIGN PATENT DOCUMENTS

| | | |
|---|---|---|
| JP | 4-321627 | 11/1992 |
| WO | WO 88/00795 | 2/1988 |
| WO | WO 88/02351 | 4/1988 |
| WO | WO 93/17693 | 9/1993 |
| WO | WO 94/00548 | 1/1994 |
| WO | WO 96/14092 | 5/1996 |
| WO | WO 97/34834 | 9/1997 |

* cited by examiner

ANTIMICROBIAL AND ANTIVIRAL COMPOSITIONS AND TREATMENTS FOR FOOD SURFACES

FIELD OF THE INVENTION

The invention relates to antimicrobial and antiviral compositions in powder or solution form containing oxidizing materials. The materials are made by reacting cooperating ingredients at controlled proportions to form an oxidant suitable for use in food applications. The oxidizing species of the invention is an in situ generated oxidant stable for limited periods, typically less than a few days, and is created from powdered materials added to an aqueous rinse or wash solution.

BACKGROUND OF THE INVENTION

Peroxygen sanitizers and halogen sanitizers are known. Peroxygen sanitizers include compounds such as hydrogen peroxide, percarboxylic acids, percarbonates, perborates, etc. These materials are relatively well characterized and understood and are commonly used in a variety of end uses. Halogen sanitizers include compounds such as hypochlorite (HOCl), chlorine dioxide ($ClO_2$), perchlorate ($HClO_4$), perbromate ($HBrO_4$), and others. These materials also have relatively well characterized compositions and properties. Halide and quaternary ammonium base sanitizers are also known. These materials are generally not considered oxidizing materials but provide limited sanitizing properties to materials. One type of halogen based sanitizers are sanitizers that can contain species such as $I_3^{-1}$, $IBrCl^{-1}$, and other similar species. Representative examples of such materials are described in Rembaum et al., U.S. Pat. No. 3,898,336; Rembaum et al., U.S. Pat. No. 3,778,476; Hollis et al., U.S. Pat. No. 4,960,590; Hollis et al., U.S. Pat. No. 5,093,078 and Dammann, European Patent Application No. 156646. These references teach isolated quaternary ammonium poly halides based on synthetic polymeric ionene (known in the industry as polymeric quats), epi-amine, and cationic acrylamide polymer resins (containing 2 or more cationic groups) precipitated with polyhalogens. Similarly, Corby, U.S. Pat. No. 4,822,513; Corby, U.S. Pat. No. 5,047,164; and Corby, U.S. Pat. No. 5,202,047 describe mixed polyhalide salts limited to 4 halogens with a maximum of one iodine or bromine atom per complex. Also, Kramer et al., U.S. Pat. Nos. 4,941,989 and 5,620,527 teach the use of antimicrobial compositions made of alkaline per-salts of quaternary ammonium compounds and hydroperoxide anions at pH's of greater than 9.5. No polyhalide counterions are utilized.

None of the aforementioned references teach the use of in-situ, labile antimicrobial compositions generated via halide salts and oxidants; especially peroxygen oxidants. All of these examples deal with stable, isolated antimicrobials that would remain in the application environment (e.g., food surface) indefinitely. Lastly, Wright et al., PCT Application No. WO 94/00548 teaches non-halogen containing quaternary ammonium compounds which are used with peracids, preferably peracetic acid. This disclosure indicates that the peracid material is activated by the presence of the quat.

Ideally, an antimicrobial agent or compound used in treating food, food preparation surfaces and utensils should have several important properties in addition to its antimicrobial efficacy. It is important that the compound or agent leave no residual antimicrobial activity. Residual activity implies the presence of a film of antimicrobial material which will continue to have antimicrobial effect and which may require further rinsing of the food product, food preparation surface, or utensils. The antimicrobial agent preferably should also be odor free to prevent transfer of undesirable odors onto the food. The antimicrobial agent should also be composed of food additive materials, or indirect or secondary direct food additive materials, which will not affect the food if contamination occurs, nor affect humans should incidental ingestion result. Further, the antimicrobial agent should preferably be composed of naturally occurring or innocuous ingredients which are chemically compatible with the environment and cause no concerns for toxic residues within the water.

The use of antimicrobial agents in the control of microorganisms is well known for various applications. For example, Grosse Bowing et al., U.S. Pat. Nos. 4,051,058 and 4,051,059 used peracetic acid as a food grade sanitizer in a variety of applications. Further, Greenspan et al., U.S. Pat. No. 2,512,640, teaches the use of a peracetic acid composition including 500 ppm or more of peracetic acid for the treatment of various fruit and vegetable compositions in a spray applicator. In the past transport and process water apparatuses have generally been treated with sodium hypochlorite and chlorine dioxide. While these materials are effective in preventing the unwanted growth of microorganisms, their use rate is very high, since they tend to be rapidly consumed by the high organic load. Further, these materials decompose, producing byproducts such as chlorites and chlorates. Hypochlorite decomposes to produce trichloromethanes which may be toxic at very low concentrations. Lastly, chlorine dioxide itself is a toxic gas.

Iodophor antimicrobial agents have also been used for various antimicrobial applications. However, iodophor compounds tend to decompose or may be lost by evaporation when used in an aqueous medium. Consequently, long-term activity requires a very high iodophor concentration.

As a result, a need exists in the food processing industry to provide antimicrobial efficacy without the toxicity problems of the past.

SUMMARY OF THE INVENTION

We have discovered a surprising effect resulting from the combination of a source of quaternary or protonizable nitrogen, an oxidant, and a halide source. More specifically, we have found that an oxidizing species is created from this combination. Since reaction is almost immediate, it is possible for aqueous or non-aqueous sanitizing processes to prepare a use solution that is available for use immediately after mixing; however, the activity is lost after a few days with reversion to harmless halide salts. It is also possible to produce solid sanitizing substrates that have residual antimicrobial and antiviral effectiveness; such as air filters or on air filters, as food packaging or plastic or cutting board additives. This oxidizing species is effective in reducing microbial and viral populations on foods, food surfaces, food wash and process waters, and food preparation surfaces and equipment as a wash liquid. This oxidizing species is also effective, by itself or mixed with other adjuvants, in reducing microbial and viral populations in other food preparation adjuncts such as in or on: air and liquid filtration equipment or filtering agents, belt sprays for food transport lines, boot and hand-wash dip-pans, food storage facilities and anti-spoilage air circulation systems, aseptic packaging sanitizing, food refrigeration and cooler cleaners and sanitizers, warewashing sanitizing, blancher cleaning and sanitizing, food packaging materials, cutting board additives, third-sink sanitizing, beverage chillers and warmers, meat chilling or scalding waters, sanitizing gels, food processing antimicrobial garment sprays, and non-to-low-aqueous food preparation lubricants, oils, and rinse additives. The oxidizing species is also effective for use in animal quarters, in animal feeds, on animal carcasses; reducing human pathogenic microbes, opportunistic or pathogenic microbes on eggs, and also in treating skin diseases on animals and mammals, or those which spread via transfer to air or surface substrates, such as disease from fungi, bacteria and viruses.

Accordingly, the invention resides in an antimicrobial and antiviral composition including in powder, liquid, gel, aerosol, or solid form: a) a source, preferably a natural one, of a quaternary or protonizable nitrogen compound; (b) an oxidant, preferably a peroxygen compound; (c) a halide source; and optionally (d) a food grade source of acidity; wherein for each part by weight of the halide source there is about 0.1 to 30 parts by weight of the nitrogen compound, about 0.1 to 40 parts by weight of the oxidant compound and about 0 to 80 parts by weight of the acidity source, and wherein a corresponding aqueous use solution of the composition has a pH of about 9 or less.

The invention further resides in a mixable, at the point of use, of a two-part liquid concentrate antimicrobial or antiviral composition suitable for treating foods, food surfaces, food wash and process waters, e.g. as above described; said composition containing in one part: (a) about 0.1 to 80 wt %, preferably about 1 to 15 wt %, of a source of a quaternary or protonizable nitrogen compound, preferably a natural source; (b) about 0.1 to 75 wt %, preferably about 1 to 20 wt % of a peroxygen compound; optionally (c) about 0 to 70 wt %, preferably about 5 to 25 wt %, of a food grade acidity source; and (d) the balance being water; and in the second part: (e) about 0.1 to 80 wt %, preferably about 1 to 15 wt %, of a halide source; (f) the balance being water. Food Grade inerts and surfactants may be added to either part.

Also, the invention resides in an antimicrobial and antiviral composition suitable for subsequent incorporation into solid, gel, aerosol, or non-aqueous liquid cleaning, sanitizing, or disinfecting products for treatment of surfaces. Thus, these include in powder, liquid, gel, or solid form: a) a source, preferably a natural one, of a quaternary or protonizable nitrogen compound; (b) an oxidant, preferably a peroxygen compound or oxidizing gas; (c) a halide source; and optionally (d) a food grade source of acidity; wherein for each part by weight of the halide source there is about 0.1 to 30 parts by weight of the nitrogen compound, about 0.1 to 40 parts by weight of the oxidant compound and about 0 to 80 parts by weight of the acidity source. The antimicrobial or antiviral composition is incorporated into the cleaning, disinfecting, or sanitizing substrate at a level of about 0.001 to 40 weight %.

The invention also resides in the powder antimicrobial or antiviral compositions suitable for incorporation (casting, absorbing, adsorbing, spray-drying, etc.,) into solid, elastomeric, or fibrous substrates for residual antimicrobial or antiviral effects.

The invention also resides in antimicrobial or antiviral compositions comprising a combination of (a) a quaternary or protonizable nitrogen compound, preferably a natural source, with (b) a polyhalogen-containing anion, and (c) a water-soluble or dispersible substrate.

The invention also resides in a solvent-free process for preparing the antimicrobial or antiviral complex by reaction of a solid or powdered quaternary or protonizable nitrogen compound, preferably a natural source, with halogen(s) and the optional application of heat and/or moisture vapors or chemical hydrates. It also encompasses solvent-free liquid complexes prepared by such a method.

The invention also resides in a method of washing and reducing microbial loadings on foods, food surfaces, food wash waters and food preparation surfaces and equipment by treating said foods and food surfaces with a dilute aqueous solution including about 0.1 to 400 grams per liter of water, preferably about 1 to 100 grams per liter of water, of the dissolved powder, solid, gel, aerosol, or liquid compositions defined above, or, in the alternative, by; (a) mixing the two part liquid concentrate as defined above in water to provide a dilute aqueous solution containing about 1 to 300 ml per liter of water, preferably 10 to 100 ml per liter of water of the total concentrate; and (b) treating said foods and food surfaces with the resulting dilute aqueous solution.

The invention also resides in treating food processing or transport waters with said liquid, gel, solid, or powdered compositions.

The invention additionally resides in treating food processing equipment and/or ware, (e.g. utensils, dishware, washware,)with said liquid, gel, aerosol, solid, or powdered compositions, or solutions containing these compositions.

The invention additionally resides in sanitizing third-sink rinse waters and utensils (e.g. bar glasses) with said liquid, gel, solid, or powdered compositions.

The invention additionally resides in treating animal quarters, surgical or treatment areas, in animal feeds, or animal carcasses; with said compositions.

The invention additionally resides in treating air streams with said compositions.

Moreover, the invention resides in the above defined methods of use wherein the antimicrobial or antiviral composition includes a complex of the formulae

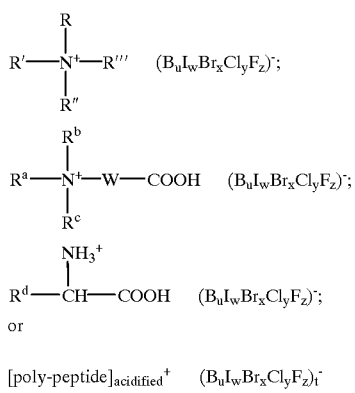

In the above formulae, R, R', R" and R'" are each independently H; a straight or branched, saturated or unsaturated hydrocarbon chain of 1–24 carbon atoms; an alkylamidoalkylene; alkylcarboxyalkylene, hydroxyalkylene or alkoxyalkylene group having 1 to 8 carbon atoms, wherein any carbon chain may be interrupted by one or more heteroatoms selected from the group consisting of nitrogen, sulfur and phosphorus;

$R^a$ is a linear or branched, saturated or unsaturated hydrocarbon, hydroxyalkyl, or alkoxyalkyl having 1–22 carbon atoms; $R^b$ and $R^c$ are independently H or $CH_3$; W is a linear or branched alkylene, hydroxyalkylene or alkoxyalkylene having 1 to 4 carbon atoms;

$R^d$ is a common moiety as part of natural amino acids, such as, for example, H, alkyl, hydroxyalkyl, thioalkyl, alkyl-aryl, carbonyl, amido, alkyl-amino, and the like.

[poly-peptide] acidified+ refers to an acidified protein, and
t is an integer greater than 0;

B is a non-halogen anion except hydroxyperoxy (–OOH);
u is an integer from 0 to 1; w is an integer from 1 to 8;
x and y are independently integers from 0 to 8, and z
is an integer from 0 to 1.

DETAILED DISCUSSION OF THE INVENTION

The invention involves an oxidizing species formed from the reaction of a source, preferably natural, of quaternary or protonizable nitrogen; an oxidant which is preferably a peroxygen compound and a halide source. The reaction is preferentially carried out in water (or alternatively in a powder or solid state with water vapor or hydrating compounds present, or with an oxidizing gas passing into the powder or solid, or a non-aqueous liquid such as a food-grade mineral oil or lecithin), and for each part by weight of the halide salt there is about 0.1 to 30 parts by weight of the quaternary or protonizable nitrogen and about 0.1 to 40 parts by weight of the oxidant compound. The antimicrobial composition includes the above materials which form the oxidizing species when reacted, and optionally about 0 to 80 parts of a food grade source of acidity. When reacted, an aqueous use solution, containing an effective amount of the resultant composition, thereof should have a pH of about 9 or less.

A number of various sources of quaternary or protonizable nitrogen can be used in the compositions of the claimed invention, although natural sources are preferred. Quaternary nitrogen sources useful in the invention include such compounds as cholines, lecithins, betaines, quaternary ammonium compounds and amine oxides.

Quaternary ammonium compounds include quaternary ammonium salts of the formula

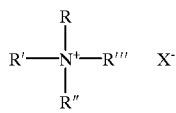

wherein X is an anion except a hydroperoxide anion; R, R', R" and R'" are each independently a straight or branched, saturated or unsaturated hydrocarbon group of 1–24 carbons; alkylamidoalkylene, hydroxyalkylene, or alkoxyalkylene groups having 1–8 carbon atoms, wherein the hydrocarbon or alkylene chain may be interrupted by one or more heteroatoms selected from the group consisting of nitrogen, sulfur, and phosphorus.

Protonizable amine compounds include the formula

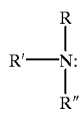

wherein R is a straight or branched alkyl group of 1–24 carbons; R' and R" are independently H, a straight or branched, saturated or unsaturated hydrocarbon group of 1–24 carbons; or R, R', and R" can each be independently alkyl-amidoalkylene, alkyl-carboxyalkylene, hydroxyalkylene, or alkoxylene groups having 1–12 carbon atoms, wherein the hydrocarbon, alkyl or alkylene chain may be interrupted by a heteroatom selected from the group consisting of nitrogen, sulfur, and phosphorus.

A nitrogen compound may also include a compound of the formula

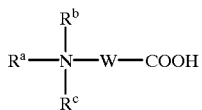

wherein $R^a$ is a linear or branched, saturated or unsaturated hydrocarbon, hydroxyalkyl or alkoxyalkyl group having 1 to 22 carbon atoms, $R^b$ and $R^c$ are independently H or $CH_3$; and W is a linear or branched alkylene, hydroxyalkylene or alkoxyalkylene group having 1–4 carbon atoms.

The above compounds are "food-grade" or "food-derived" or GRAS, or allowed by the Food and Drug administration as indirect, or secondary direct, food additives. Typically available and pictured below is the structure of choline. Lecithin is structurally similar in having the same trimethyl nitrogen terminal group, but the rest of the molecule is a mixed glycerol ester containing phosphorous. In fact, lecithin is also known as phosphatidyl choline.

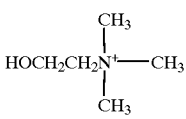

Additional preferred quaternary nitrogen sources include a choline, particularly a choline chloride, a choline bitartrate, an acetyl choline; or mixtures thereof. Additional preferred compounds are betaine, cetyl pyridinium chloride and, phospholipids such as the lecithins (including phosphatidyl choline.), sphingomyelin, and the cephalins. The nitrogen source may also include mixtures thereof.

The invention can also make use of protonizable nitrogen sources which are not natural quaternary compounds. Examples include proteins, amino acids, amine oxides and amines which can form acid salts and mixtures thereof. Generally, these can be characterized as:

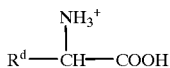

and

[poly-peptide]$_{acidified}{}^+$ wherein $R^d$ is a common moiety as part of natural amino acids; e.g., H, alkyl, hydroxyalkyl, thioalkyl, alkyl-aryl, carboxyl, amido, alkyl-amino, and the like; [poly-peptide]$_{acidified}{}^+$ is intended to define an acidified polypeptide, such as an acidified protein.

These include, for example, sarcosine, taurine, and glycine, which are preferred in the invention and which are pictured below, respectively:

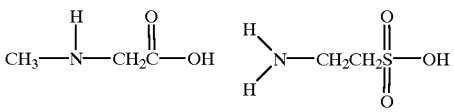

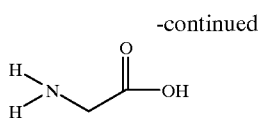

Protonizable simple proteins such as albumins, phosphoproteins, protamines, histones, chromoproteins, schleroproteins, glutenins and globulins are also examples of protonizable nitrogen sources useful in the present invention. Examples of protonizable proteins include milk, whey or whey protein, egg, blood and plant (e.g., corn or wheat glutens) proteins. The nitrogen compound can be a protein, an acid salt thereof, or a mixture of proteins and their corresponding acid salts. Other useful protonatable nitrogen sources include proline derivatives, pyrrolidine derivatives, and porphin derivatives.

A wide range of oxidants including peroxygen compounds known to those of skill in the art can be used. It is possible to utilize oxidants such as hypochlorites, chlorates, permanganates, nitrates or nitric acid, etc.; or gaseous oxidants such as ozone, oxygen, chlorine dioxide, chlorine, sulfur dioxide, etc.; however, preferred compounds include hydrogen peroxide and various peroxycarboxylic acids. Solid chlorites, hypochlorites and nitrates may be used alone or in combination. Especially preferred for solid formulae are percarbonates or persulfates, wherein the carbonate or sulfate themselves are not essentially oxidized but instead act as a substrate for the peroxygen complex. Most preferred is sodium percarbonate in solid formulations; however, gaseous oxidants are useful for non carbonate containing compositions. For liquid compositions, hydrogen peroxide or peracetic acid are the preferred oxidants; however, food grade hypochlorites, chlorites, or ozone might also be employed for in-situ preparations. Ultimately, any oxidant that can convert the halide source into its complexed form is acceptable; however, food-grade oxidants are generally employed.

There are a large number of possible halide sources—such as metal or ammonium halides, haloforms or other organic halogens, or elemental halogens—useful in the claimed invention. Preferred metal halides include alkali metal halides, preferably iodide salts of the formula $MI_n$, wherein M is a metal ionic species and n is a number equal to the metal valence. Preferred alkali metals are sodium and potassium. Other preferred halides include bromides and chlorides. A preferred salt is potassium iodide, cuprous iodide or a mixture thereof. A preferred embodiment uses a metal halide salt containing a mixture of halide salts where at least one is an iodide salt. Another preferred embodiment uses a single metal halide salt which is an iodide or bromide salt. Yet another preferred embodiment uses an ammonium salt. Natural or prepared sources containing halides such as sea water, kelp, table salt, etc., are also valuable.

The combination of a nitrogen compound, oxidant and halide source forms in situ a complex.

Such includes a complex of the formula

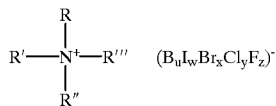

wherein R, R', R" and R'" are each independently H, a straight or branched, saturated or unsaturated, hydrocarbon group of 1–24 carbons, alkylamidoalkylene, alkylcarboxyalkylene, hydroxyalkylene, or alkoxylene groups having 1–8 carbon atoms, wherein any carbon chain may be interrupted by one or more heteroatoms selected from the group consisting of nitrogen, sulfur, and phosphorus; u is an integer from 0 to 1; w is an integer from 1 to 8; x and y are each independently integers from 0 to 8; z is an integer from 0 to 1; and B is a non-halogen anion, except hydroperoxy such as, for example, sulfate, methylsulfate, ethylsulfate, borate, phosphate, carbonate, silicate, tartrate, acetate, citrate, and the like.

Alternatively, there may be included a complex of the formula

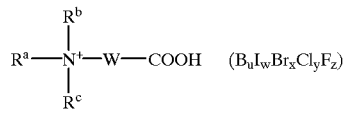

wherein $R^a$ is a linear or branched, saturated or unsaturated, hydrocarbon, hydroxyalkyl or alkoxyalkyl group having 1–22 carbon atoms; $R^b$ and $R^c$ are independently H or $CH_3$; W is a linear or branched alkylene, hydroxyalkylene or alkoxyalkylene group having 1–4 carbon atoms; and B, u, w, x, y and z are as defined above.

Alternatively, there may be included a complex of the formula

wherein $R^d$ is a common moiety as part of natural amino acids; e.g., H, alkyl, hydroxyalkyl, thioalkyl, alkyl-aryl, carboxyl, amido, alkyl-amino, and the like; and B, u, w, x, y and z are as defined above.

Alternatively, there may be included a complex of the formula

wherein $[polypeptide]^+_{acidified}$ is a protonated simple or complex poly-amino acid or protein, and (t) is an integer greater than 0; and B, u, w, x, y and z are as defined above.

The aqueous solution of the invention is characterized by a yellow to red to brown color which serves as an indicator of solution effectiveness. As long as the color remains, the solution retains good killing properties. This time period is about 50 hours for the use solution; however, shorter or longer life times can be formulated.

The invention can also include, if necessary, an acid component for controlling the use solution pH. This is necessary for enhanced microbial reduction; probably because the amine compound must be in its cationic or slightly neutralized form to form the labile, in-situ complex. The exact pH necessary will depend on the identity of the amine involved but, preferably, should be about 8 or less. Since the invention involves a food grade wash composition, the composition can include a food grade acid such as phosphoric acid, malic acid, tartaric acid, citric acid, acetic acid, etc. In the powder composition, the source of acidity might include one or more of the GRAS food acids listed in the Code of Federal Registry (CFR) in 21 CFR 173, 182 and 184 or 40 CFR 180, such as, for example, citric acid, glutamic acid, sorbic acid, benzoic acid, succinic acid, and the like. Alternatively, the source of acidity can include a food grade acid salt such as sodium diacetate, mono-or-dibasic calcium, potassium, or sodium phosphate. Additionally, carbonation acidification via the interaction of carbon dioxide with water is possible for aqueous formulations.

The invention also includes food grade, or naturally derived or food surface compatible, wetting and detersive agents allowed for direct food addition or secondary direct food washing; specifically those wetting agents listed in 21 CFR sections 182, 194 and 173, or alternatively in 40 CFR 180, such as, for example, linoleic acid, sorbitan esters, sugar esters, lecithins and ethoxylated lecithins, PEG alkylates, linear alkylbenzene sulfonate, stearyl citrate, alkyl naphthalene sulfonates, Pluronics® surfactants and various short-chain fatty acids. The wetting agents are typically not necessary for affecting the microbial reduction, but are present for detersive and surface tension reduction reasons; however, some may be employed as part of the synergistic, in-situ, antimicrobial and antiviral formula.

Likewise, the inerts found in the aforementioned CFR sections might be added as fillers, buffers, thickeners, viscosity modifiers, anticaking agents, etc. For example, formulations have been prepared with: sodium chloride, sodium bicarbonate, magnesium sulfate, dried ox bile, sucrose, carnuba wax, tricalcium silicate, corn gluten, starch, and cellulosic derivatives. According to the claimed invention, use compositions are: 1) solutions which are aqueous solutions, 2) solutions which are non-aqueous using food-grade components which are liquid or form liquids, or 3) solids or powders containing a source, preferably natural, of quaternary or protonizable nitrogen, an oxidant which is preferably a peroxide compound, a halide source, and optionally a food grade acid component. We have discovered that a ternary weight ratio between the three reactive ingredients can range from 1:1:1 to 1:5:1 to 1:15:15 to 1:1:15 for the nitrogen compound, peroxygen and halide source respectively. An optimal range is 1:3:1 to 1:3:3.

The single-phase antimicrobial and antiviral compositions of the invention are preferably powdered, liquid, or solid mixtures which can be added directly to an aqueous rinse or wash liquid. These aqueous antimicrobial solutions have many uses. For example, they can be used to wash food products such as fresh fruits and vegetables prior to being processed or served. This can consist of a tank or tub of the aqueous antimicrobial solution, into which the food products are dunked prior to use. Alternatively, fresh fruits and vegetables could be sprayed with an antimicrobial solution according to the invention. These solutions could even be used in grocery store misting systems. On a larger scale, these solutions can be used as transport streams used to move large quantities of fruit within a processing facility. These antimicrobial and antiviral solutions can also be used to reduce microbial populations on food preparation surfaces and utensils. While conventional treatments can be used on these surfaces, use of the claimed compositions prevent problems with contamination of food products as a result of incomplete rinsing of surfaces. The antimicrobial solutions used in treating foods and food preparation surfaces, equipment and utensils typically have about 0.1 to 400 grams of antimicrobial composition per liter of water, preferably about 1 to 100 grams per liter.

The powder or single-phase non-aqueous liquid antimicrobial and antiviral compositions of the invention can also be added into other powder or solid wash products for later addition to a sanitizing or disinfecting solution; or for incorporation into woven, extruded, or molded substrates for residual sanitizing effects. The antimicrobial or antiviral compositional powders would typically be incorporated into other substrates or products at a level of 0.001 to about 40 weight %.

The two part liquid concentrate of the invention can also be used in the above situations. Preferably, the two part concentrate is mixed to provide a dilute aqueous solution of about 0.1 to 130,000 ppm of the total concentrate; wherein the foods and food surfaces are treated with the dilute aqueous solution.

These compositions (either powdered or two-part liquid) can be used to reduce the microbial and viral count of water used in the production of foods, beverages, and bottled water products. This involves adding small but effective amounts of the composition to the production water. Specifically, foods and food surfaces can be treated with a dilute aqueous solution having about 0.1 to 400 grams per liter, preferably about 1 to 100 grams per liter, of the composition described. The food surface can be a clean-in-place system. 5 The compositions described above can also be used to reduce the microbial or viral count on animals or animal carcasses, said method including treating said animals or animal carcasses with a dilute aqueous solution of the composition. The compositions can also be used to reduce human pathogenic microbes on animals and to reduce opportunistic pathogenic microbes on living eggs.

The compositions described can also be used to reduce microbes and odors in animal feeds and to reduce microbes, viruses, and odors in animal watering stations, enclosures, and animal surgical or treatment areas. These methods include treating said stations and enclosures with an effective amount of the complex described above.

These compositions can also be used to treat skin diseases of—or on—animals or mammals (or mammalian diseases conveyed to a surface, such as skin or hard surfaces, by physical contact or air transmission), by applying to the skin of said animal or mammal an effective amount of the composition. The skin disease in question can be, for example, athletes foot fungus or hairy hoof wart disease. Alternatively, the disease can be a skin or transmittable viral disease such as parvovirus, coxsackie or herpes. The disease can also be a mycobacterial or bacterial type, such as tuberculosis or Legionella.

These compositions can also be used to reduce microbial and viral counts in air and liquids by incorporation into filtering media or breathing filters.

Foods, food surfaces, food packages, food preparation components, mammals, mammalian habitats, and air—as described above—can be treated to reduce the microbial or viral count present by washing with a solution made from mixing the compositions described above with water to provide a dilute aqueous solution of about 0.1 to 130,000 ppm of the total concentrate; and treating said foods and food surfaces with the resulting dilute aqueous solution. The food surface in question can be a counter or cutting board, a clean-in-place system, a clean-out-of-place system, a ware wash machine, a sink or other washing or sanitizing vessel, or a food package or preparation or transport surface. The mammalian surface in question can be the skin or a hard surface or air stream which has been contacted by the mammal.

The microbial or viral count on foods, food surfaces, or mammals can be reduced by treating said foods and food, or mammalian, surfaces with a dilute aqueous solution having about 0.1 to 400 grams per liter of an antimicrobial and antiviral composition including a complex of the formula

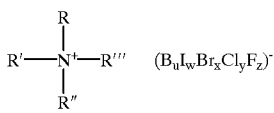

wherein R, R', R", R'", B, u, w, x, y and z are as defined above; and optionally a food grade source of acidity.

The microbial or viral count of water used in the production or transport of foods, beverages, and bottled water products can be reduced by adding to said water an antimicrobial and antiviral composition including a complex of the formula

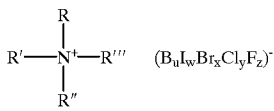

wherein R, R', R", R'", B, u, w, x, y and z are as defined above; and optionally a food grade source of acidity.

The microbial or viral count on foods, food surfaces, or mammals can be reduced by treating said foods and food, or mammalian, surfaces with a dilute aqueous solution having about 0.1 to 400 grams per liter of an antimicrobial and antiviral composition including a complex of the formula

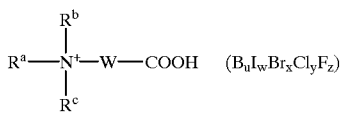

wherein $R^a$, $R^b$, $R^c$, B, u, W, w, x, y and z are as defined above; and optionally a food grade source of acidity.

The microbial or viral count of water used in the production or transport of foods, beverages, and bottled water products can be reduced by adding to said water an antimicrobial and antiviral composition having a complex of the formula

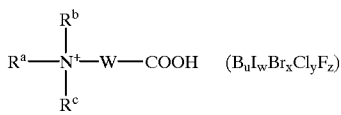

wherein $R^a$, $R^b$, $R^c$, B, u, W, w, x, y and z are as defined above; and optionally a food grade source of acidity.

The microbial or viral count on foods, food surfaces, or mammals can be reduced by treating said foods and food, or mammalian, surfaces with a dilute aqueous solution having about 0.1 to 400 grams per liter of an antimicrobial and antiviral composition including a complex of the formula

wherein $R^d$, B, u, w, x, y and z are as defined above; and optionally a food grade source of acidity.

The microbial or viral count of water used in the production or transport of foods, beverages, and bottled water products can be reduced by adding to said water an antimicrobial and antiviral composition having a complex of the formula

wherein $R^d$, B, u, w, x, y and z are as defined above; and optionally a food grade source of acidity.

The microbial or viral count on foods, food surfaces, or mammals can be reduced by treating said foods and food, or mammalian, surfaces with a dilute aqueous solution having about 0.1 to 400 grams per liter of an antimicrobial and antiviral composition including a complex of the formula

$$[\text{poly-peptide}]^+_{acidified}\ (B_uI_wBr_xCl_yF_z)_t^-$$

wherein $[\text{polypeptide}]^+_{acidified}$, B, u, w, x, y, z, and t are as defined above; and optionally a food grade source of acidity.

The microbial or viral count of water used in the production or transport of foods, beverages, and bottled water products can be reduced by adding to said water an antimicrobial and antiviral composition having a complex of the formula

$$[\text{poly-peptide}]_{acidified}^+\ (B_uI_wBr_xCl_yF_z)_t^-$$

wherein [polypeptide], B, u, w, x, y, z, and t are as defined above; and optionally a food grade source of acidity.

By way of illustration, typical powdered, non-aqueous liquid, gel, aerosol, or solid formulation ranges are:

| Component | Useful Wt-% | Preferred Wt-% | More Preferred Wt-% |
|---|---|---|---|
| nitrogen source | 1–20 | 2–15 | 3–10 |
| oxidant compound | 1–40 | 3–20 | 4–10 |
| metal halide | 1–40 | 1–15 | 2–10 |
| acidity source | 0–80 | 20–50 | 30–40 |
| wetting agents | 0–20 | 0–10 | 0–5 |
| inerts | 0–80 | 0–40 | 0–30 |

The present invention also includes as an alternative embodiment a two part liquid concentrate where each part contains an aqueous concentrate including a nitrogen source, an oxidant compound, preferably a peroxygen compound and optionally an acidity source in part (a) and a metal halide in part (b); and optionally, inerts and wetting agents. Typical two part liquid formulation ranges are:

| Component | Useful Wt-% | Preferred Wt-% | More Preferred Wt-% |
|---|---|---|---|
| first part | | | |
| nitrogen source | 0.1–80 | 0.5–50 | 1–15 |
| oxidant compound | 0.1–75 | 1–35 | 10–20 |
| acidity source | 0–70 | 5–50 | 5–25 |
| wetting agents | 0–10 | 0.05–5 | 0.1–1 |
| inerts | 0–50 | 0–20 | 0–10 |
| water | balance | balance | balance |

| Component | Useful Wt-% | Preferred Wt-% | More Preferred Wt-% |
|---|---|---|---|
| second part | | | |
| metal halide salt | 0.1–80 | 0.5–30 | 1–15 |
| wetting agents | 0–10 | 0.05–5 | 0.1–1 |
| inerts | 0–50 | 0–20 | 0–10 |
| water | balance | balance | balance |

When used, a total actives concentration ranging from 10 to 100,000 ppm is preferred. Typical product use concentration ranges for either a liquid, gel, aerosol, powder, or solid composition are given in the table below:

| Component | Useful (ppm) | Preferred (ppm) | More Preferred (ppm) |
|---|---|---|---|
| nitrogen source | 1–10,000 | 10–5,000 | 20–1,000 |
| oxidant compound | 1–30,000 | 30–15,000 | 50–1,500 |
| acidity source | 0–20,000 | 30–5,000 | 50–1,000 |
| metal halide salt | 1–30,000 | 10–15,000 | 20–1,500 |
| wetting agents | 0–5,000 | 0–500 | 0–100 |
| inerts | 0–50,000 | 0–10,000 | 0–1,000 |

The following examples are provided to further illustrate the present invention and are not limiting thereon. Example powdered formulations are shown below:

| Compound | Wt-% |
|---|---|
| Formula I | |
| choline chloride | 1.5 |
| sodium percarbonate (12.5% $H_2O_2$) | 25.0 |
| sodium bicarbonate | 24.0 |
| citric acid | 48.0 |
| potassium iodide | 1.5 |
| Formula II | |
| betaine | 3.0 |
| sodium percarbonate (12.5% $H_2O_2$) | 40.0 |
| sodium acid phosphate | 10.0 |
| sorbic acid | 7.0 |
| citric acid | 30.0 |
| cuprous iodide | 10.0 |
| Formula III | |
| choline bitartrate | 4.0 |
| sodium percarbonate (12.5% $H_2O_2$) | 30.0 |
| sodium chloride | 10.0 |
| malic acid | 5.0 |
| sorbic acid | 5.0 |
| citric acid | 35.0 |
| potassium iodide | 2.0 |
| lecithin | 2.0 |
| magnesium sulfate | 7.0 |
| Formula IV | |
| taurine | 3.0 |
| sodium percarbonate (12.5% $H_2O_2$) | 40.0 |
| sodium diacetate | 40.0 |
| sodium acid phosphate | 15.0 |
| potassium iodide | 2.0 |
| Formula IVb | |
| choline chloride | 1.3 |
| sodium percarbonate (12.5% $H_2O_2$) | 18.8 |
| sodium diacetate | 38.6 |
| citric acid | 38.6 |
| potassium iodide | 2.7 |
| Formula V | |
| milk protein | 1.0 |
| sodium percarbonate (10.0% $H_2O_2$) | 35.0 |
| citric acid | 40.0 |
| sodium chloride | 21.0 |
| cuprous iodide | 3.0 |
| Formula VI | |
| lecithin | 5.0 |
| sodium nitrate | 40.0 |
| citric acid | 40.0 |
| sorbitan stearate | 4.0 |
| sodium iodide | 10.0 |
| starch | 1.0 |
| Formula VII | |
| choline chloride | 1.5 |
| sodium percarbonate (12.5% $H_2O_2$) | 36.0 |
| sodium acid phosphate | 10.0 |
| potassium iodide | 1.5 |
| sodium sulfate | 51.0 |
| Formula VIIb | |
| choline chloride | 1.3 |
| sodium percarbonate (12.5% $H_2O_2$) | 18.8 |
| sodium acid phosphate | 25.8 |
| potassium iodide | 2.6 |
| citric acid | 51.5 |
| Formula VIIc | |
| choline chloride | 1.3 |
| sodium percarbonate (12.5% $H_2O_2$) | 18.8 |
| sodium acid phosphate | 77.3 |
| potassium iodide | 2.6 |

EXAMPLE 2

Phase Liquid Compositions:

| Formula # | First Part Component | Wt-% | Second Part Component | Wt-% |
|---|---|---|---|---|
| VIII | choline chloride | 2.0 | cuprous iodide | 2.5 |
| | hydrogen peroxide | 5.0 | sodium bromide | 1.0 |
| | sodium 2-ethylhexyl sulfate | 0.1 | sodium sulfate | 6.0 |
| | phosphoric acid | 8.0 | water | balance |
| | water | balance | | |
| IX | lecithin | 2.0 | potassium iodide | 2.0 |
| | hydrogen peroxide | 6.0 | water | balance |
| | citric acid | to pH = 3.0 | | |
| | water | balance | | |
| X | didecyl dimethyl ammonium chloride | 2.0 | potassium iodide | 10.0 |
| | hydrogen peroxide | 15.0 | water | balance |
| | citric acid | to pH < 8 | | |
| | water | balance | | |

-continued

| Formula # | First Part Component | Wt-% | Second Part Component | Wt-% |
|---|---|---|---|---|
| XI | didecyl dimethyl ammonium chloride | 0.1 | potassium iodide | 1.0 |
|  | peracetic acid | 0.8 | water | balance |
|  | hydrogen peroxide | 4.1 |  |  |
|  | water | balance |  |  |
| XII | didecyl dimethyl ammonium chloride | 0.1 | potassium iodide | 1.0 |
|  | peracetic/peroctanoic acids | 0.8 | water | balance |
|  | hydrogen peroxide | 4.1 |  |  |
|  | water | balance |  |  |
| XIII | choline chloride | 2.0 | sodium iodide | 10.0 |
|  | hydrogen peroxide | 15.0 | water | balance |
|  | citric acid | to pH = 3 |  |  |
|  | water | balance |  |  |
| XIV | C8 dimethyl amine oxide | 10.0 | sodium iodide | 10.0 |
|  | hydrogen peroxide | 30.0 | water | balance |
|  | optional acid | to pH < 8 |  |  |
|  | water | balance |  |  |
| XV | choline chloride | 5.0 | sodium iodide | 5.0 |
|  | hydrogen peroxide | 15.0 | water | balance |
|  | optional acid | to pH < 8 |  |  |
|  | water | balance |  |  |
| XVb | choline chloride | 0.7 | potassium iodide | 1.5 |
|  | hydrogen peroxide, 35% | 4.0 | water | balance |
|  | phosphoric acid | 5.0 |  |  |
|  | water | balance |  |  |

Example Solid Block Compositions:

| Compound | Wt-% |
|---|---|
| Solid Block Formula XVI | |
| choline chloride | 1.5 |
| sodium percarbonate (12.5% $H_2O_2$) | 25.0 |
| sodium bicarbonate | 24.0 |
| citric acid | 24.0 |
| potassium dihydrogen phosphate | 24.0 |
| potassium iodide | 1.5 |
| Solid Block Formula XVII | |
| choline chloride | 1.6 |
| sodium percarbonate (12.5% $H_2O_2$) | 4.5 |
| citric acid | 62.5 |
| dipotassium hydrogen phosphate | 30.8 |
| potassium iodide | 0.6 |
| Solid Block Formula XVIII | |
| choline chloride | 4.8 |
| hydrogen peroxide, 35% | 24.8 |
| sodium tripolyphosphate | 60.8 |
| potassium iodide | 9.6 |
| Non-Aqueous Liquid Formula XIX | |
| lecithin | 23.8 |
| mineral oil | 71.4 |
| iodine | 4.8 |

WORKING EXAMPLE #1

We have discovered that in situ antimicrobial compositions can be evidenced by certain attributes; for example, color, pH, and UV absorption. Tables 1 and 2 show various ternary and quaternary compositions of the claimed invention, along with single and binary control compositions.

Table 2 also demonstrates that a variety of food-source nitrogen compounds are usable in the claimed invention.

TABLE 1

| Composition | Choline[a]:$H_2O_2$:KI:acid ratio | Resultant pH | Resultant Color | UV Maximum |
|---|---|---|---|---|
| Single and Binary Component Controls | | | | |
| 1 Choline[a] | 1:0:0:0 | 5.8 | colorless | none |
| Choline:$H_2O_2$ | 1:1:0:0 | 5.8 | colorless | none |
| Choline:KI | 1:0:1:0 | 5.8 | colorless | none |
| Lecithin | 1:0:0:0 | 6.3 | colorless | none |
| Lecithin:$H_2O_2$ | 1:1:0:0 | 6.0 | colorless | none |
| Lecithin:KI | 1:0:1:0 | 6.5 | colorless | none |
| 2 $H_2O_2$ | 0:1:0:0 | 5.6 | colorless | none |
| 3 KI | 0:0:1:0 | 5.9 | colorless | none |
| 4 $H_2O_2$:KI | 0:1:1:0 | 6.7 | faint yellow | 295 nm |
| Ternary Compositions | | | | |
| 5 Choline:$H_2O_2$:KI | 1:1:1:0 | 7.1 | yellow | 295, 365 nm |
|  | 1:1:2:0 | 7.4 | yellow | 295, 365 nm |
|  | 1:2:1:0 | 7.1 | yellow | 295, 365 nm |
|  | 2:1:1:0 | 7.2 | yellow | 295, 365 nm |
|  | 1:1:6:0 | 7.6 | yellow | 295, 365 nm |
|  | 1:6:1:0 | 6.8 | yellow | 295, 365 nm |
|  | 6:1:1:0 | 6.9 | yellow | 295, 365 nm |
| Quaternary Compositions | | | | |
| 6 Choline:$H_2O_2$:KI:acid | 1:1:1:0.2 | 4.0 | bright yellow | mostly 365 nm |
|  | 1:1:6:0.2 | 4.0 | bright yellow | mostly 365 nm |
|  | 1:6:1:0.2 | 4.0 | bright yellow | mostly 365 nm |
|  | 6:1:1:0.2 | 4.0 | bright yellow | mostly 365 nm |

[a]Choline = choline chloride
[b]Acid = acetic acid

WORKING EXAMPLE #2

Table 2 shows similar color formation and UV-VIS results to Table 1 using a variety of permanent or protonizable quaternary entities. Again, the evidence of the yellowish color and UV-VIS absorptions are found using the compositions of the present invention; in contrast to the control or prior art compositions.

TABLE 2

| Composition | Nitrogen[1]:$H_2O_2$:KI:acid (wt:wt:wt:wt) | Composition Color | UV-VIS Maximum |
|---|---|---|---|
| Binary and Tertiary Component Controls | | | |
| 1 choline chloride | 1:0:0:0.2 | colorless | none |
| lecithin | 1:0:0:0.2 | colorless | none |
| protein[2] | 1:0:0:0.2 | colorless | none |
| sarcosine | 1:0:0:0.2 | colorless | none |
| glycine | 1:0:0:0.2 | colorless | none |
| protein[3] | 1:0:0:0.2 | colorless | none |
| KI | 0:0:1:0.2 | faint yellow | 295 nm only |
| $H_2O_2$ | 0:1:0:0.2 | colorless | none |
| POAA[4] | 0:0:1:1.5 | colorless | none |

TABLE 2-continued

| Composition | Nitrogen[1]:$H_2O_2$: KI:acid (wt:wt:wt:wt) | Composition Color | UV-VIS Maximum |
|---|---|---|---|
| $H_2O_2$/OA/POAA[5] | 0:1:0:1.0 | colorless | none |
| QUAT[6]: POAA[4] | 0.2:1:0:1.5 | colorless | none |
| QUAT[6] | 1.0:0:0:1.0 | colorless | none |
| choline chloride:KI | 1:0:1:0.2 | colorless | none |
| choline chloride:$H_2O_2$ | 1:1:0:0.2 | colorless | none |
| lecithin:KI | 1:0:1:0.2 | colorless | none |
| lecithin:$H_2O_2$ | 1:1:0:0 | colorless | none |
| Various Nitrogen Compositions[a] | | | |
| 2 choline chloride | 1:1:1:0.2 | bright yellow | 365 nm + 295 nm |
| lecithin | 1:1:1:0.2 | bright yellow | 365 nm + 295 nm |
| protein[c] | 1:1:1:0.2 | bright yellow | 365 nm + 295 nm |
| sarcosine | 1:1:1:0.2 | bright yellow | 365 nm + 295 nm |
| glycine | 1:1:1:0.2 | bright yellow | 365 nm + 295 nm |
| protein[d] | 1:1:1:0.2 | bright yellow | 365 nm + 295 nm |

[1]Nitrogen = natural source of quaternary or protonizable nitrogen.
[2]Protein source from vegetable mix.
[3]Protein source from blood.
[4]POAA = peroxyacetic acid blend; Ecolab Inc., St. Paul, MN
[5]$H_2O_2$/OA/POAA = hydrogen peroxide/octanoic/peroxyacetic acid blend; Ecolab Inc., St. Paul, MN
[6]Quat = didecyl dimethyl ammonium chloride.

It is shown in Table 1 that mixing certain acidic ternary combinations of a food-derived quaternary nitrogen compound, plus and iodine salt and hydrogen peroxide, results in a pH higher than any of the single components. In Table 1, experiment 6 and Table 2 experiment 2 where the pH is buffered to below 5, the pH rise does not occur, but the in-situ color formation does occur. Note also the bright yellow color formed in all the nitrogen compositions in experiments 5 and 6 of Table 1 and in experiment 2 of Table 2. Conversely, none of the single or binary combinations yield the colored in-situ composition. It will be demonstrated later that these compositions possess strong antimicrobial activity. The yellow color is an indication of the antimicrobial activity of the composition. It is also noteworthy that the yellowish color formation is evidenced by the UV-visible absorbance at 365 nm; and is in obvious contrast to no absorbance or the free iodide absorbance at 295 nm; demonstrating the unique in-situ complex. Note also that the addition of a small amount of acid as seen in experiment 2 of Table 2 and experiment 5 of Table 1 results in an increase in the intensity of the yellow color.

WORKING EXAMPLE #2

Table 3 demonstrates the chemical uniqueness of the present invention compared to known embodiments with regards to UV absorbance. The results verify the different chemical moieties present. The free iodine at 295 nm is evidenced in many of the samples, but the distinctive differentiating absorbances are also indicated. The present invention is conclusively evidenced by the absorbance maximum at 365 nm.

Table 3 also demonstrates the uniqueness of the present invention over that taught by Kramer et al., in U.S. Pat. Nos. 4,941,989 and 5,620,527, which teach the use of antimicrobial compositions made of alkaline per-salts of quaternary ammonium compounds and hydroperoxide anions at pH's of greater than 9.5.

TABLE 3

| Composition | Actives | UV max |
|---|---|---|
| Prior Art | | |
| 1 Divosan MH[a] | interhalogens | 295 nm and 305 nm |
| 2 Mikroklene[i] | $I_2$ | 295 nm |
| 3 WO 94/00548 | quats/peracids | none |
| 4 Oxy-Brite[i] | $H_2O_2$ | none |
| 5 Ster-Bac-Blu[i] | quat halide | none |
| 6 U.S. Pat. No. 5,620,527 and U.S. Pat. No. 4,941,989 | quat hydroperoxide[b] | 278 nm |
| 7 U.S. Pat. No. 5,620,527 and U.S. Pat. No. 4,941,989 | iodized quat hydroperoxide[c] | none |
| 8 U.S. Pat. No. 5,620,527 and U.S. Pat. No. 4,941,989 | iodized quat hydroperoxide[d] | mainly 288 nm, some 352 nm |
| 9 U.S. Pat. No. 5,620,527 and U.S. Pat. No. 4,941,989 | quat hydroperoxide[e] | 278 nm |
| Present Invention | | |
| 10 1[f] | pH = 7 complex | equal 295 nm and 365 nm |
| 11 2[g] | pH = 4 complex | mostly 365 nm |
| 12 3[h] | pH = 3 complex | mostly 365 nm |

[a]Divosan MH is described in U.S. Pat. Nos. 4,822,513; 5,047,164; and 5,202,047; Diversey Corporation, Plymouth, MI.
[b]Ultra-Kleen HW; The Sterilex Corporation; Owings Mills, MD.
[c]As per U.S. Pat. Nos. 5,620,527 and 4,941,989 using choline chloride and with iodide added.
[d]As per U.S. Pat. Nos. 5,620,527 and 4,941,989 using ADBAC quats with iodide added.
[e]Ultra-Kleen liquid; The Sterilex Corporation; Owings Mills, MD.
[f]1 is example 5 from Table 1.
[g]2 is example 6 from Table 1.
[h]3 is formula example II.
[i]Ecolab Inc., St. Paul, MN.

WORKING EXAMPLE #3

Tables 4 and 5 demonstrate various 2 part liquid formulations according to the invention. Results recorded include the pH of the solution, the color of the solution and the log reduction in microbe. In Table 4, *E. coli* is used in all examples, while a variety of organisms (gram positive and gram negative bacteria, a yeast, a mold) are used in Table 5.

TABLE 4

| Composition | Nitrogen: $H_2O_2$:KI (wt:wt:wt) | pH | Composition Color | E. Coli Log Reduction[b] |
|---|---|---|---|---|
| Single Component Controls[c] | | | | |
| 1 choline chloride | 1:0:0 | 3 | colorless | 0 |
| lecithin | 1:0:0 | 3 | colorless | 0 |
| $H_2O_2$ | 0:1:0 | 3 | colorless | 0.2 |
| KI | 0:0:1 | 3 | colorless | 0 |
| Ternary Compositions | | | | |
| 2 choline:$H_2O_2$:KI | 3:1:1 | 3 | bright yellow | >5.2 |
| choline:$H_2O_2$:KI | 3:1:1 | 5 | bright yellow | >5.2 |
| lecithin:$H_2O_2$:KI | 3:1:1 | 3 | bright yellow | >5.2 |
| lecithin:$H_2O_2$:KI | 3:1:1 | 5 | bright yellow | 4.9 |
| lecithin:$H_2O_2$:KI | 3:1:1 | 9 | colorless | 0 |

[a]Nitrogen = natural source of quaternary or protonizable nitrogen.
[b]Log Reduction vs. an untreated control, 30 second contact time.
[c]Not including added acid or base for pH adjustment.

TABLE 5

| Composition | | N-source: $H_2O_2$:KI (ppm:ppm:ppm) | pH | Composition Color | Microbe | Log Reduction[b] |
|---|---|---|---|---|---|---|
| *Compositional Controls[c]* | | | | | | |
| 1 | $H_2O_2$ | 0:300:0 | 5 | colorless | *E. coli* | 0.2 |
| | $H_2O_2$ | 0:300:0 | 5 | colorless | *S. aureus* | 0.4 |
| | $H_2O_2$ | 0:532:0 | 3 | colorless | *Z. bailii* | 0.1 |
| | $H_2O_2$ | 0:532:0 | 5 | colorless | *Z. bailii* | 0.1 |
| | $H_2O_2$ | 0:532:0 | 7 | colorless | *Z. bailii* | 0.1 |
| | $H_2O_2$ | 0:532:0 | 5 | colorless | *P. expansum* | 0.0* |
| | $H_2O_2$:KI | 0:250:250 | 5 | colorless | *P. expansum* | 1.2* |
| | KI | 0:0:500 | 5 | colorless | *P. expansum* | 0.0* |
| 2 | choline chloride | 300:0:0 | 7 | colorless | *E. coli* | 0.0 |
| | | 300:0:0 | 7 | colorless | *Z. bailii* | 0.0 |
| | QUAT (didecyl dimethyl ammonium chloride) | 100:0:0 | 7 | colorless | *P. expansum* | 1.0* |
| | | 20:0:0 | 3 | colorless | *Z bailii* | 0.1 |
| | | 20:432:0 | 3 | colorless | *Z. bailii* | 0.1 |
| *Ternary Compositions* | | | | | | |
| 3 | choline:$H_2O_2$:KI | 100:300:100 | 3 | yellow | *S. aureus* | >5.2 |
| | choline:$H_2O_2$:KI | 100:300:100 | 5 | yellow | *S. aureus* | >4.7 |
| | lecithin:$H_2O_2$:KI | 100:300:100 | 3 | yellow | *S. aureus* | >4.7 |
| | lecithin:$H_2O_2$:KI | 100:300:100 | 5 | yellow | *S. aureus* | 4.9 |
| | lecithin:$H_2O_2$:KI | 100:300:100 | 7 | colorless | *S. aureus* | 0.0 |
| | lecithin:$H_2O_2$:KI | 100:300:100 | 9 | colorless | *S. aureus* | 0.0 |
| | lecithin:$H_2O_2$:KI | 100:25:100 | 3 | yellow | *E. coli* | 3.1 |
| | lecithin:$H_2O_2$:KI | 100:100:100 | 3 | yellow | *E. coli* | 5.2 |
| | lecithin:$H_2O_2$:KI | 100:500:100 | 3 | yellow | *E. coli* | 5.9 |
| | lecithin:$H_2O_2$:KI | 100:300:100 | 7 | colorless | *E. coli* | 0.3 |
| | mix[d]:$H_2O_2$:KI | 100:300:100 | 3 | yellow | *S. aureus* | >5.2 |
| | mix[d]:$H_2O_2$:KI | 100:300:100 | 5 | yellow | *S. aureus* | 4.4 |
| | mix[d]:$H_2O_2$:KI | 100:300:100 | 3 | yellow | *E. coli* | >5.2 |
| | mix[d]:$H_2O_2$:KI | 100:300:100 | 5 | yellow | *E. coli* | 3.8 |
| | choline:$H_2O_2$:KI | 100:300:100 | 3 | yellow | *Z. bailii* | >6.0 |
| | betaine:$H_2O_2$:KI | 100:300:100 | 7.6 | yellow | *E. coli* | 3.6 |
| | QUAT (didecyl dimethyl ammonium chloride) | 50:150:50 | 7 | yellow | *P. expansum* | >4.6* |

[a]Nitrogen = natural source of quaternary or protonizable nitrogen.
[b]Log Reduction vs. an untreated control, 30 second contact time except (*) = 15 minute contact time.
[c]Not including added acid or base for pH adjustment.
[d]An equal weight percent mix of lecithin and choline chloride.

As shown in the two Tables, there is a direct correlation between color of the solution and microbial efficacy. In this we are defining a lack of microbial efficacy to be less than a 0.5 log reduction, while effectiveness is being defined as greater a than 1.0 log reduction. Looking at Table 4, there is an obvious direct correlation between color and antimicrobial activity. Table 5 demonstrates the same correlation. Further, Table 5 indicates that the most effective pH appears to be below about 9, with a preferred pH range of 3 to 5.

WORKING EXAMPLE #4

Working Example 4 is directed to comparing the antimicrobial activity of the two-part liquid compositions of the invention to known compositions for microbial reductions on food surfaces. Specifically, comparison is made to the use of either sodium hypochlorite (bleach), hydrogen peroxide or peracetic acid.

Testing was performed on commercial Roma tomato surfaces using the test organism *Salmonella javinia*. For the pathogenic organisms, a 1:10 dilution of a $10^7$ CFU/ml (colony forming units per ml) test system suspension was prepared. Whole tomatoes were placed into a plastic bag, and each bag was inoculated with a 10-mil. test system suspension, resulting in an inoculum level of $10^7$ CFU/ml. Bags are gently shaken for even distribution of the test system for five minutes. The produce types are then stored overnight at 4° C. Untreated controls were also prepared. Two-liter volumes of the test solutions were prepared in 4-liter beakers. Solutions were prepared in laboratory tap water to simulate industry conditions. The tomatoes were then exposed to the test solution by submersion for five minutes at 72° F. (about 22° C.). At the end of that time, the tomatoes were removed from the solution and thoroughly rinsed under fresh-running tap water. Fifty grams of the home produce (tomato), plus 100 ml buffered dilution water were placed into a stomacher bag. The tomatoes were massaged for 60 seconds. Cereal dilutions were made and planted on TGE (Salmonella). Plates were incubated at 35° C. for 48 hours.

TABLE 6

| Test # | Test Organism | Active Antimicrobial (ppm) | Treatment Process | Log Reduction |
|---|---|---|---|---|
| | Known | | | |
| 1 | S. javiana | 0 ppm[b] | untreated control[b] | 0.0 |
| | S. javiana | 30 ppm | sodium hypochlorite | 0.3 |
| 2 | S. javiana | 80 ppm | sodium hypochlorite | 1.9 |
| 4 | S. javiana | 80 ppm | hydrogen peroxide | <0.1 |
| 5 | S. javiana | 80 ppm | peracetic acid | 2.8 |
| | Present Invention | | | |
| 6 | S. javiana | 50 ppm | lecithin, $H_2O_2$, KI | 1.1 |
| 7 | S. javiana | 50 ppm | choline, lecithin, $H_2O_2$, KI | 2.5 |

[a]Log Reduction versus the untreated control.
[b]A control experiment using no antimicrobial agent.

These results show comparable effectiveness of the compositions of the present invention versus conventional commercial chemical treatments of sodium hypochlorite or peracetic acid treatment systems for affecting microbial reductions on food surfaces.

WORKING EXAMPLE #5

Working Example 5 is similar to the previous example in that comparisons are made between the present invention and known commercial compositions for control of microorganisms on food surfaces. In this case, however, comparisons were made for meat carcass treatments.

Testing was performed on prerigor beef surfaces from a packing house. Total bacterial flora were tested. The carcasses were treated for 30 seconds and drained for 10 minutes. Test samples were isolated and plated for total call in the former units.

TABLE 7

| Test # | Treatment Process | Active Antimicrobial | Log Reduction[a] |
|---|---|---|---|
| | Known | | |
| 1 | lactic acid | 5000 ppm | 0.8 |
| 2 | cetyl pyridinium chloride | 1000 ppm | 0.5 |
| 3 | Citrex[b] | 1880 ppm | 0.7 |
| 4 | fatty acid blend[c] | 500 ppm | 1.7 |
| 5 | peracid[d] | 500 ppm | 1.4 |
| | Present Invention | | |
| 6 | cetyl pyridinium chloride + $H_2O_2$ + KI | 50 ppm | 2.0 |

[a]Log Reduction relative to the untreated starting meat carcass.
[b]Commercial product from Citrex, Inc.; Miami, Florida.
[c]Commercial product from Ecolab, Inc.; St. Paul, MN using C8/C10 fatty acids.
[d]Commercial product from Ecolab, Inc.; St. Paul, MN using C2/C8 peracids.

The results of Table 7 demonstrate the remarkably improved effectiveness of the current composition versus the conventional chemical treatments. Log reductions for the present composition was above any of the commercial treatments while using ten to one hundred times lower concentrations of actives.

WORKING EXAMPLE #6

The data of table 8 illustrates the microbial reduction effectiveness of a powdered formula according to the present invention. The powder composition of Formula I previously described) was tested for microbial efficacy. Six grams of the powdered formula was dissolved into one gallon of water containing 500 ppm of synthetic hardness (equal mix of calcium and magnesium carbonates) and the resultant solution was tested for efficacy against Esherichia coli (E. coli) ATCC 1129 at various time periods after preparation. Thirty second exposure times were used, and the microbial platings were performed per Ecolab Microbiological Services SOP method MS009 (reference: AOAC Method 960.09); i.e., thirty second exposure times were used and 1 mL of the test substance/microorganism mixture was transferred into 9.0 mL of neutralizer for a $10^{-1}$ dilution. Subsequent dilutions were made using sterile phosphate buffered dilution water to yield dilutions of $10^{-3}$, and $10^{-5}$. Pour plate technique was utilized with Tryptone Glucose Extract agar and plates were incubated at 37° C. for 48 hours.

The results demonstrate the extended efficacy of the powder formula against the common food or water contaminant E. coli, even in the presence of considerable water hardness. This result was surprising since it is common knowledge in the art that hardness ions severely interfere with conventional quaternary ammonium halide antimicrobials. No detrimental effect was found in the formula of the present invention. The previously demonstrated correlation between color, titratable actives, and microbial kill is seen again; i.e., no color or titratable actives yield no microbial reduction, while titratable actives and color correspond to reduction. The actives were titrated using an Ecolab test kit #101 using thiosulfate to titrate active iodine levels at 1 ppm per drop of titrant. The formula mix time and microbial testing was not followed to a time that would demonstrate a loss in log reduction with loss in titratable actives; however, the next example using a more tenacious microbe will show this expected result.

TABLE 8

| Formula Mix Time[1] (hours) | Solution Color | Titratable Active[2] (ppm) | Microbial Counts (CFU/ml) | Log Reduction[3] (E. coli) |
|---|---|---|---|---|
| 0 | colorless | 0 | $6 \times 10^7$ | 0 |
| 0.1 | yellow | 10 | <10 | 6.9 |
| 8 | yellow | 15 | <10 | 6.9 |
| 24 | yellow | 20 | <10 | 7.0 |
| 32 | yellow | 20 | <10 | 7.0 |
| 48 | yellow | 12 | <10 | 7.0 |

[1]The time elapsed after mixing the formula powder into the test solution.
[2]Titratable active oxidant using test kit #101.
[3]Relative to an untreated control standard using SOP#MS009.

WORKING EXAMPLE #7

As in example 6, the data of Table 9 illustrates the microbial reduction effectiveness of a powdered formula according to the present invention. The test protocol of example 6 was used and the resultant solution was tested for efficacy against Staphylococcus aureus ATCC 6538, another common human pathogen on food matter or in wash waters.

Again, the results demonstrate the microbial efficacy of the powder compositions. Additional, they teach the correlation between reduction effectiveness and titratable actives; i.e., ranging from no reduction with 0 titratables, to near 4-log reduction with 20 ppm titratables, and then back to near 3-log reduction with 12 ppm. This demonstrates the gaussian kill profile of the formula with the desired fall-off of actives over time.

TABLE 9

| Formula Mix Time[1] (hours) | Solution Color | Titratable Active[2] (ppm) | Microbial Counts (CFU/ml) | Log Reduction[3] (S. aureus) |
|---|---|---|---|---|
| 0 | colorless | 0 | 6 × 10[7] | 0 |
| 0.1 | yellow | 10 | 5 × 10[5] | 2.1 |
| 8 | yellow | 15 | 4 × 10[4] | 3.2 |
| 24 | yellow | 20 | 9 × 10[3] | 3.9 |
| 32 | yellow | 20 | 1 × 10[4] | 3.7 |
| 48 | yellow | 12 | 5 × 10[4] | 3.2 |

[1]The time elapsed after mixing the formula powder into the test solution.
[2]Titratable active oxidant using test kit #101.
[3]Relative to an untreated control standard using SOP #MS009.

WORKING EXAMPLE #8

Table 10 demonstrates the utility of the present invention for reducing food spoilage. A liquid emulsion Formula VII was prepared using 0.1 wt % lecithin, 0.1 wt % KI, 0.3 wt % hydrogen peroxide with the balance being water; then the pH was adjusted to 3.0 with citric acid. Roma tomatoes were dipped into the solution for 15 seconds, rinsed with distilled water for 15 seconds, wiped dry with a cotton tissue, and stored at room temperature for 1 week; with non-dipped tomatoes used as a control.

The results demonstrate the ability of the present compositions to aid in spoilage and shrink reduction for food products.

TABLE 10

| Experiments | Tomato Odors (after 1 week) | Tomato Surface Visuals (after 1 week) |
|---|---|---|
| untreated controls | musty rot | extensive shriveling and rot, cavitated stem top with blackening, gray fuzzy mold over the surface. |
| Formula VII treated | none | some wrinkling with no rot, no cavitation or blackening, no visible mold. |

WORKING EXAMPLE #9

The data of Table 11 illustrates the microbial reduction effectiveness of various solid and 2-part liquid compositions for sanitizing food preparation or consumption utensils in a sink; as styled in the restaurant industry as "third-sink-sanitizing" applications.

The previously described powder compositions of Formula I, and the liquid compositions IX–XIV, were prepared and tested for: evidencing color formation, titratable active components using a chlorine equivalence (as per kitchen health standard guidelines), and microbial efficacy. The indicated dosages were dissolved into one gallon of water and the resultant solutions were tested for efficacy as per active oxidant using test kit #101, visual production of the yellowish indicating color, and microbial plating.

The results indicated the developing onset of the yellow color, a titratable active component forming over time, and an appreciable microbial reduction for a variety of microorganisms including gram positive and gram negative bacteria and a yeast. Again, and equally important, is the previously considered resiliency to hardness ions which are known to severely interfere with conventional quaternary ammonium halide antimicrobials. No detrimental effect was found in the present compositions.

TABLE 11

| Test Composition | Added Weight (grams) | Solution Color[1] | 30 Minute Titratable Active[2] (ppm) | Microbe Tested | [30 Second] Log Reduction[3] |
|---|---|---|---|---|---|
| powder I | 4.2 | t = 0, colorless; t = 5 min., yellow; t = 30 min., yellow | 20 ppm | E. coli | >5.2 |
| powder 1 | 4.2 | t = 0, colorless; t = 5 min., yellow; t = 30 min., yellow | 20 ppm | S. aureus | >4.7 |
| liquid IX | 18.9 | t = 0, colorless; t = 5 min., yellow; t = 30 min., yellow | — | E. coli | >7.0 |
| liquid X | 3.8 | t = 0, colorless; t = 5 min., yellow; t = 30 min., yellow | 49 ppm | Z. bailii | >6.0 |
| liquid XI | 37.9 | t = 0, colorless; t = 5 min., yellow; t = 30 min., yellow | 120 ppm | Z. bailii | >4.7 |
| liquid XII | 37.9 | t = 0, colorless; t = 5 min., yellow; t = 30 min., yellow | 125 ppm | Z. bailii | >4.7 |
| liquid XIII | 3.8 | t = 0, colorless; t = 5 min., yellow; t = 30 min., yellow | 45 ppm | Z. bailii | >6.0 |
| liquid XIV | 3.8 | t = 0, colorless; t = 5 min., yellow; t = 30 min., yellow | — | E. Coli | 6.0 |

[1]The time elapsed after mixing the formula powder into the test solution.
[2]Titratable active oxidant using test kit #101.
[3]Relative to an untreated control standard using SOP #MS009; using a 30 second exposure time after 5 minutes of complex formation.

WORKING EXAMPLE #10

Table 12 compares formulas of the present invention with prior art examples of food-preparation hard surface sanitizing. The results demonstrate the compositions according to the present invention to be comparable, or better, in microbial efficacy to those of the prior art, while utilizing a lower level of total actives.

TABLE 12

| Product Name | Composition Actives | Actives Conc. (ppm)[1] | Log Reduction S. aureus | E. coli |
|---|---|---|---|---|
| Prior Art | | | | |
| 1 Hydrogen Peroxide | $H_2O_2$ | 300 | 0.4 | 0.2 |
| 2 Vortexx[3] | $H_2O_2$/OA/POAA | 95 | 5.4 | 3.1 |
| 3 Ster-Bac Blue[4] | QUAT chlorides | 98 | 5.8 | 0.8 |
| 4 Ultra-Kleen ™ Liquid[5] | [QUAT-HO2] | 781 | 5.4 | 3.1 |
| 5 Virucidal Extra[6] | unknown | 1:400[7] | 1.2 | 0.3 |
| Present Invention | | | | |
| 6 powder Formula VII | $H_2O_2$/QUAT/KI | 50[8] | >6.0 | >5.2 |
| 7 liquid Formula IX | $H_2O_2$/QUAT/KI[9] | 50[8] | >6.0 | >5.2 |

[1]Active Concentrations based on use recommendations from supplier labels.
[2]30 second exposure reductions of E. coli ATCC 11229.
[3]A synergistic blend of hydrogen peroxide/octanoic/peroxyacetic acid blend; Ecolab Inc., St. Paul, MN
[4]A quaternary ammonium chloride blend; Ecolab Inc., St. Paul, MN
[5]A quaternary hydroperoxide blend; The Sterilex Corp.; Owings Mills, MD; U.S. Pat. Nos. 5,620,527 and 4,941,989.
[6]A broad spectrum virucide, bactericide, fungicide; AVS (N.I.); Newtownards, CO. DOWN; G.B. 9406046-2.
[7]The actives levels are unknown so the use dilution is listed.
[8]Based on $I_2$ conversion equivalency.

WORKING EXAMPLE #11

Table 13 demonstrates virucidal efficacy of the compositions of the present invention; and compares these results with four commercial virucidal products. The results demonstrate the substantial virucidal efficacy of the "food-grade" composition versus the prior art; as defined by the difference between the virus titer and the virucidal test being greater than $10^3$, for use against *Canine parvovirus* and other human or animal viral agents and pathogens (especially those of naked-DNA or naked-RNA types).

TABLE 13

| Product Name | Actives Conc. (ppm)[1] | *Canine parvovirus* ATCC VR-935 Virucidal Result $ID_{50}^2$ | Virucidal Efficacy ($>10^3$ required)[3] |
|---|---|---|---|
| Prior Art | | | |
| 1 Vortexx[4] | 380 | $10^{2.5}$ | $10^2$ |
| 2 Ultra-K1een ™ Liquid[5] | 6250 | $10^{3.5}$ | $10^1$ |
| 3 Virucidal Extra[6] | 1:100[8] | $10^{2.5}$ | $10^2$ |
| 4 Virkon S[7] | 1:100[8] | $10^{2.5}$ | $10^2$ |
| Present Invention | | | |
| 5 Solid Formula XVI | 60[9] | $10^{4.7}$ | $<10^2$ |
| 6 Solid Formula XVI | 120[9] | $10^{2.5}$ | $10^4$ |
| 7 Solid Formula XVI | 240[9] | $10^{2.5}$ | $10^4$ |

[1] Active Concentrations based on use recommendations from supplier labels.
[2] 10 minute exposure time; $ID_{50}$ calculated according to the Reed-Muench equation.
[3] The difference between the virus titer control and the virucidal test result; $>10^3$ needed for virucidal efficacy.
[4] A synergistic blend of hydrogen peroxide/octanoic/peroxyacetic acid blend; Ecolab Inc., St. Paul, MN
[5] A quaternary hydroperoxide blend; The Sterilex Corp.; Owings Mills, MD; U.S. Pat. Nos 5,620,527 and 4,941,989
[6] A broad spectrum virucide, bactericide, fungicide; AVS (N.I.); Newtownards, CO. DOWN; G.B. 9406046-2.
[7] A broad spectrum virucide, bactericide, fungicide; Antec International; Sudbury, Suffolk, England; GB 2164851.
[8] The actives levels are unknown so the use dilution is listed.
[9] Based on $I_2$ conversion equivalency.

WORKING EXAMPLE #12

Table 14 compares the virucidal efficacy of the composition of the present invention, toward parvoviruses in general, with published results against *Feline parvovirus*. The results indicate a 10–40× reduction in actives to produce kill versus the published prior art.

TABLE 14

| Viral Agent | Minimum Concentration (for 10-minute inactivation)[1] |
|---|---|
| NaOCl | 2,000 ppm |
| IPA | 500,000 ppm |
| Ethanol | 500,000 ppm |
| Benzyl Quats | 5,000 ppm |
| A33 Dry[2] | 1,800 ppm (failed) |
| Iodophor (as $I_2$) | 5,000 ppm (1-log) |
| o-phenylphenol G | 100,000 ppm |
| Glutaraldehyde | 10,000 (2-log) |
| Solid Formula XVI | 600 ppm product (120 ppm actives) |

[1] "Disinfection, Sterilization, and Preservation" Lea & Febiger; Philadelphia, PA; 1991 p.413.
[2] Quaternary ammonium chloride blend; Ecolab Inc.,; St. Paul, MN

WORKING EXAMPLE #13

The data of Table 15 demonstrates the storage stability, for effecting microbial reduction, of a powdered formula (Formula I) according to the present invention; i.e., storage stability of the current invention while in a powder form. The test protocol of example 6 was used, except using 12 grams per gallon of the powder Formula I, and the resultant solution was tested for efficacy against *Staphylococcus aureus* ATCC 6538.

The results of Table 15 demonstrate the microbial efficacy of the powder compositions, even over an extended storage time.

TABLE 15

| Formula VIIb Powder Age[1] (days) | Solution Color | 30 second Log Reduction[2] (*S. aureus*) |
|---|---|---|
| 0 days | yellow | 0 |
| 15 days | yellow | >6.8 |
| 30 days | yellow | >6.9 |
| 150 days | yellow | >6.8 |

[1] The aging time elapsed from the production date of a powder Formula I.
[2] Relative to an untreated control standard using SOP #MS009.

WORKING EXAMPLE #14

An antimicrobial wash powder for use in reducing microbial counts on food matter, in food process waters, warewash machines, and third-sink sanitizing was made by mixing together, at ambient temperature: 77.3 g sodium dihydrogen phosphate, 18.8 g sodium percarbonate, 2.6 g KI, and 1.3 g choline chloride to afford a white powder. Dilution of 0.4 g powder in 1000 g water afforded a pale yellow solution with a pH of 6.6 which is effective for food washing and wash waters.

WORKING EXAMPLE #15

A germicidal block for use in reducing microbial counts on food matter, in food process waters, warewash machines, and third sink sanitizing was made by mixing together, at ambient temperature: 724.9 g sodium tripoly phosphate, 57.0 g choline chloride, 1 15.0 g KI, and while still mixing, adding 295.9 g hydrogen peroxide [35% active] dropwise to minimize effects of strong exotherm which develops. At end of peroxide addition, product was a dark orange, damp powder which was transferred to a mold for solidification. Solidification to a very hard block occurred within 1 minute of transfer to the mold. Flushing or spraying water over block affords a pale yellow solution which is effective for food washing, wash waters, and sanitizing.

WORKING EXAMPLE #16

A germicidal block for use in reducing microbial counts on food matter, in food process waters, warewash machines, and third sink sanitizing was made by mixing together, at ambient temperature: 724.9 g sodium tripoly phosphate, 57.0 g choline chloride, 115.0 g KI, and while still mixing, adding 295.9 g hydrogen peroxide [35% active] dropwise to minimize effects of strong exotherm which develops. At end of peroxide addition, product was a dark orange, damp powder which was transferred to a mold for solidification. Solidification to a very hard block occurred within 1 minute of transfer to the mold. Flushing or spraying water over block affords a pale yellow solution which (with a titratable residual and the distinctive 365 nm peak for the complex) is effective for food washing, wash waters, and sanitizing.

WORKING EXAMPLE #17

A germicidal oil-soluble for use in reducing microbial counts on food matter, in food process waters, warewash machines, third sink sanitizing, non-aqueous lubricants, and mammalian skin surfaces was made by mixing together, at ambient temperature: 30 grams of a hydrophobic oil (like food-grade mineral oil, linoleic acid, or soy oil), 10.0 g lecithin, and 2.0 g iodine. Almost immediately the typifying yellow color of the active composition forms. The formulation can be thickened with common thickeners. It is used as a non-aqueous treatment, or subsequently added to other products as an antimicrobial or antiviral additive.

WORKING EXAMPLE #18

The germicidal powder of Formula VIIb for use in reducing microbial counts on food matter, in food process waters, warewash machines, third sink sanitizing, and veterinarian applications was made by mixing together, at ambient temperature: 193.25 g sodium dihydrogen phosphate, 193.25 g citric acid, 94.00 g sodium percarbonate, 13.00 g potassium iodide, and 6.50 g choline chloride. Mixed together the formula yields a white powder with yellow & brown particles. Mixing 6 grams per gallon of the formula into water yields a yellow color after 30 seconds with the distinctive 365 nm peak corresponding to the claimed active.

WORKING EXAMPLE #19

A germicidal block for use in reducing microbial counts, as described in the earlier examples, is made by mixing together at ambient temperature 127.55 g dipotassium hydrogen phosphate, 258.95 g citric acid, 18.80 g sodium percarbonate, 2.60 g potassium iodide, and 6.50 g choline chloride; followed by placing the mix into a block mold and into a 120° F. oven for 12 hours to solidify to a hard, light orange, block. Flushing or spraying water over the block affords a pale yellow solution (with a titratable residual and the distinctive 365 nm peak for the complex) which is effective for food washing, wash waters, and sanitizing.

WORKING EXAMPLE #20

A germicidal powder for use in reducing microbial counts on food matter, in food process waters, warewash machines, third sink sanitizing, and veterinarian applications was made by mixing together, at ambient temperature: 38.65 g citric acid, 38.65 g sodium diacetate, 18.8 g sodium percarbonate, 1.3 g potassium iodide, and 1.3 g choline chloride. Mixed together the formula yields a white powder. Mixing 6 grams per gallon of the formula into water yields a yellow color after 30 seconds with the distinctive 365 nm peak corresponding to the claimed active.

WORKING EXAMPLE #21
Preparation of Choline Tetraiodochloride:

Mixed together 50.18 g choline chloride and 91.3 g iodine at ambient temperature. As the desired complex formed during mixing, the white powder of the choline chloride and the gray flakes of the iodine became a dark brown liquid. It was unexpected that a cationic material such as our target product was a solvent-free liquid rather than a solid.

WORKING EXAMPLE #22
Preparation of Choline Diiodochloride:

Mixed together 100.0 g choline chloride and 181.6 g iodine at ambient temperature. As the desired complex formed during mixing, the white powder of the choline chloride and the gray flakes of the iodine became a dark brown liquid. It was unexpected that a cationic material such as our target product was a solvent-free liquid rather than a solid.

WORKING EXAMPLE #23

A germicidal block for use in reducing microbial counts is made by mixing together at 70° C. 9.8 g Grindsted Citrem N12 [stearyl citrate; supplier: Danisco] and 0.2 g of the choline diiodochloride made in example #22; followed by placing the mix into a block mold and cooling to room temperature to a hard, light orange, block. Flushing or spraying water over the block affords a pale yellow solution (with a titratable residual and the distinctive 365 nm peak for the complex) which is effective for food washing, wash waters, and sanitizing.

WORKING EXAMPLE #24

A germicidal block for use in reducing microbial counts is made by melting together at about 60° C. 16.3 g polyethylene glycol (PEG) 6000 distearate and 0.3 g of the choline diiodochloride—as made in example #22—followed by placing the mix into a block mold and cooling to room temperature to a hard, tan block. Flushing or spraying water over the block affords a pale yellow solution (with a titratable residual and the distinctive 365 nm peak for the complex) which is effective for food washing, wash waters, and sanitizing.

WORKING EXAMPLE #25

A germicidal block for use in reducing microbial counts is made by melting together at about 60° C. 50.0 g polyethylene glycol (PEG) 6000 distearate, 14.5 g citric acid, and 1.5 g of the choline diiodochloride—as made in example #22—followed by placing the mix into a block mold and cooling to room temperature to a hard, yellow block. Flushing or spraying water over the block affords a pale yellow solution (with a titratable residual and the distinctive 365 nm peak for the complex) which is effective for food washing, wash waters, and sanitizing.

WORKING EXAMPLE #26

A germicidal block for use in reducing microbial counts is made by melting together at about 60° C. 50.0 g polyethylene glycol (PEG) 6000 distearate, 14.5 g citric acid, and 1.5 g of the choline diiodochloride—as made in example #22—followed by placing the mix into a block mold and cooling to room temperature to a hard, yellow block. Flushing or spraying water over the block affords a pale yellow solution (with a titratable residual and the distinctive 365 nm peak for the complex) which is effective for food washing, wash waters, and sanitizing.

WORKING EXAMPLE #27

A germicidal block for use in reducing microbial counts is made by mixing without heat 41.43 g trisodium phosphate dodecahydrate, 10.00 g citric acid, and 2.00 g of the choline diiodochloride—as made in example #22—followed by pressing the mix into a block mold and cooling to room temperature to a hard, white block. Flushing or spraying water over the block affords a pale yellow solution (with a titratable residual and the distinctive 365 nm peak for the complex) which is effective for food washing, wash waters, and sanitizing.

WORKING EXAMPLE #28
Preparation of Choline Dibromochloride:

Mixed together in the absence of solvent to afford an orange-red gel: 8.28 g choline chloride and 4.73 g bromine. The gel can be used as a surface antimicrobial, or as an additive to other compositions and products.

WORKING EXAMPLE #29
Preparation of Choline Tetrabromochloride:

Mixed together in the absence of solvent to afford an orange-red liquid: 1.72 g choline chloride and 1.96 g bromine. The solventless liquid can be used as a surface antimicrobial, or as an additive to other compositions and products. Especially useful is to deposit the pre-made complex onto a water soluble or dispersible substrate for rapid water release.

WORKING EXAMPLE #30
Preparation of Choline Tetraiodochloride:

Mixed together in the absence of solvent and warmed gently for a few minutes in a 120F oven to afford a solvent-free, dark brown liquid: 5.0 g choline chloride, 18.1 g iodine. The solventless liquid can be used as a surface antimicrobial, or as an additive to other compositions and products. Especially useful is to deposit the pre-made complex onto a water soluble or dispersible substrate for rapid water release.

WORKING EXAMPLE #31
Preparation of Choline Hexaiodochloride:

Mixed together in the absence of solvent and warmed gently for a few minutes in a 120F oven to afford a solvent-free, dark brown liquid: 5.0 g choline chloride and 27.2 g iodine. The solventless liquid can be used as a surface antimicrobial, or as an additive to other compositions and products. Especially useful is to deposit the pre-made complex onto a water soluble or dispersible substrate for rapid water release.

WORKING EXAMPLE #32
Preparation of Choline Octaiodochloride:

Mixed together in the absence of solvent and warmed gently for a few minutes in a 120F oven to afford a solvent-free, dark brown liquid: 5.0 g choline chloride, 36.3 g iodine. The solventless liquid can be used as a surface antimicrobial, or as an additive to other compositions and products. Especially useful is to deposit the pre-made complex onto a water soluble or dispersible substrate for rapid water release.

The above specification, examples and data provide a complete description of the manufacture and use of the composition of the invention. Since many embodiments of the invention can be made without departing from the spirit and scope of the invention, the invention resides in the claims hereinafter appended.

We claim:

1. An antimicrobial and antiviral composition comprising in powder, non-aqueous liquid, gel, aerosol, or solid form:
   (a) a source of a nitrogen compound which is acceptable on foods, wherein the nitrogen compound is selected from the group consisting of a phosphatidyl choline, choline chloride, choline tartrate, choline acetate, and a mixture thereof;
   (c) a halide source comprising a metal halide salt, a halogen or a mixture thereof, wherein said halide or halogen comprises at least a bromine or iodine atom; and
   (d) optionally a food grade source of acidity;
   wherein an aqueous solution thereof has a pH of about 9 or less and an ultraviolet absorption maximum at about 365 nm.

2. The composition of claim 1, wherein for each part by weight of the halide source there is about 0.1 to 30 parts by weight of the nitrogen compound, about 0.1 to 40 parts by weight of the oxidant and about 0 to 80 parts by weight of the acidity source.

3. The composition of claim 1, wherein the oxidant is a percarbonate.

4. The composition of claim 1, wherein the oxidant is hydrogen peroxide.

5. The composition of claim 1, wherein the oxidant is a peroxycarboxylic acid.

6. The composition of claim 1, wherein the oxidant is a gas selected from the group consisting of ozone, sulfur dioxide, oxygen, chlorine, and chlorine dioxide.

7. The composition of claim 1, wherein the oxidant is a chlorite, hypochlorite, nitrate salt, or a mixture thereof.

8. The composition of claim 1, wherein the halide source is a salt, or mixture thereof, of the formula:

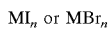

wherein M is a metal ionic species and n is a number equal to the metal valence.

9. The composition of claim 1, wherein the halide source is an alkali metal halide salt.

10. The composition of claim 1, wherein the halide source comprises at least two moles of iodide or bromide for every one mole of chloride.

11. The composition of claim 8, wherein the halide source is potassium iodide, cuprous iodide, or a mixture thereof.

12. The composition of claim 1, wherein the source of acidity is an acid selected from the group consisting of malic acid, tartaric acid, citric acid, glutaric acid, sorbic acid, benzoic acid, succinic acid, and a mixture thereof.

13. The composition of claim 12, wherein the source of acidity is citric acid.

14. The composition of claim 1, wherein the source of acidity comprises a food grade acid salt.

15. The composition of claim 14, wherein the food grade acid salt is sodium diacetate or mono-or-dibasic potassium or sodium phosphate.

16. The composition of claim 1, wherein the composition further comprises food grade inerts and surfactants.

17. A two part liquid antimicrobial concentrate composition comprising in one part:
   (a) about 0.1 to 80 wt % of a natural source of a quaternary or protonizable nitrogen compound which is acceptable on foods, wherein said nitrogen compound is selected from the group consisting of:
   (i) a compound of the formula

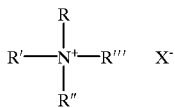

wherein X is an anion except a hydroperoxide anion; R, R', R" and R'" are each independently H; a straight or branched, saturated or unsaturated, hydrocarbon group of 1–24 carbons; an alkylamidoalkylene, alkylcarboxyalkylene, hydroxyalkylene, or alkoxyalkylene group having 1–8 carbon atoms, wherein the hydrocarbon, alkyl or alkylene chain may optionally be interrupted by one or more heteroatoms selected from the group consisting of nitrogen, sulfur, and phosphorus;
   (ii) a protein, an acid salt thereof, or a mixture of proteins and their corresponding acid salts;

(iii) an acidified polypeptide compound of the formula

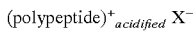

wherein (polypeptide)$^+_{acidified}$ is a protonated simple or complex poly-amino acid or protein, and X$^-$ is an anion except a hydroperoxide anion;

(iv) a compound of the formula

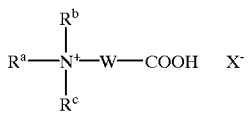

wherein R$^a$ is a linear or branched, saturated or unsaturated, hydrocarbon, hydroxyalkyl or alkoxyalkyl group having 1–22 carbon atoms; R$^b$ and R$^c$ are independently H or CH$_3$; W is a linear or branched alkylene, hydroxyalkylene or alkoxyalkylene group having 1–4 carbon atoms, and X is an anion except a hydroxyperoxide anion;

(v) an amino acid compound of the formula

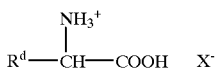

wherein R$^d$ is a side chain of a natural amino acid moiety, and X$^-$ is an anion except a hydroxyperoxide anion;

(vi) a protonizable nitrogen source selected from the group consisting of sarcosine, taurine and a mixture thereof; and (vii) a nitrogen compound selected from a C$_8$–C$_{18}$ alkyl pyridinium ammonium salt and phosphatidyl choline, choline chloride, choline tartrate, choline acetate, and a mixture thereof;

(b) about 0.1 to 75 wt % of an oxidant;

(c) about 0.1 to 75 wt % of a food grade acidity source; and (d) the balance being water; and in the second part:

(e) about 0.1 to 80 wt % of a halide source comprising a metal halide salt, a halogen or a mixture thereof, wherein said halide or halogen comprises at least a bromine or iodine atom;

(f) the balance being water.

18. The composition of claim 17, wherein the nitrogen compound is of the formula

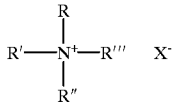

wherein X is an anion except a hydroperoxide anion;

R, R', R" and R'" are each independently H; a straight or branched, saturated or unsaturated, hydrocarbon group of 1–24 carbons; an alkylamidoalkylene, alkylcarboxyalkylene, hydroxyalkylene, or alkoxyalkylene group having 1–8 carbon atoms, wherein the hydrocarbon, alkyl or alkylene chain may optionally be interrupted by one or more heteroatoms selected from the group consisting of nitrogen, sulfur, and phosphorus.

19. The composition of claim 17, wherein the nitrogen compound is a protein, an acid salt thereof, or a mixture of proteins and their corresponding acid salts.

20. The composition of claim 17, wherein the nitrogen compound is an acidified polypeptide compound of the formula

wherein [polypeptide]$^+_{acidified}$ is a protonated simple or complex poly-amino acid or protein, and X$^-$ is an anion except a hydroperoxide anion.

21. The composition of claim 20, wherein the acidified polypeptide is derived from milk, whey or whey protein, egg, blood and corn or wheat glutens.

22. The composition of claim 17, wherein the nitrogen compound is a compound of the formula

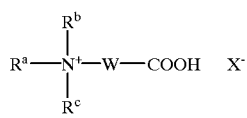

wherein R$^a$ is a linear or branched, saturated or unsaturated, hydrocarbon, hydroxyalkyl or alkoxyalkyl group having 1–22 carbon atoms; R$^b$ and R$^c$ are independently H or CH$_3$; W is a linear or branched alkylene, hydroxyalkylene or alkoxyalkylene group having 1–4 carbon atoms, and X is an anion except a hydroxyperoxide anion.

23. The composition of claim 17, wherein the nitrogen compound is an amino acid compound of the formula

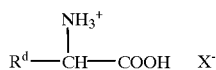

wherein R$^d$ is a side chain of a natural amino acid moiety, and X$^-$ is an anion except a hydroxyperoxide anion.

24. The composition of claim 17, wherein the nitrogen compound is a protonizable nitrogen source selected from the group consisting of glycine, sarcosine, taurine and a mixture thereof.

25. The composition of claim 17, wherein the nitrogen compound is a C$_8$–C$_{18}$ alkyl pyridinium ammonium salt, phosphatidyl choline, choline chloride, choline tartrate, choline acetate, or a mixture thereof.

26. The composition of claim 25, wherein the nitrogen compound is a cetyl pyridinium salt.

27. The composition of claim 17, wherein the oxidant is a percarbonate.

28. The composition of claim 17, wherein the oxidant is hydrogen peroxide.

29. The composition of claim 17, wherein the oxidant is a peroxycarboxylic acid.

30. The composition of claim 29, wherein the peroxycarboxylic acid is peroxyacetic acid.

31. The composition of claim 17, wherein the oxidant is ozone, chlorine dioxide, sulfur dioxide, chlorine, a hypochlorite salt, a nitrate salt, a chlorite salt or a mixture of said salts.

32. The composition of claim 17, wherein the halide source is a salt, or mixture thereof, of the formula:

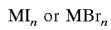

wherein M is a metal ionic species and n is a number equal to the metal valence.

33. The composition of claim 17, wherein the halide source comprises an alkali metal halide salt.

34. The composition of claim 17, wherein the halide source comprises a mixture of halide salts having at least one iodide salt.

35. The composition of claim 32, wherein the halide source is potassium iodide, cuprous iodide, or a mixture thereof.

36. The composition of claim 17, wherein the source of acidity comprises a food grade acid selected from the group consisting of phosphoric acid, acetic acid, malic acid, tartaric acid, citric acid, and a mixture thereof.

37. The composition of claim 17, wherein the source of acidity comprises an acid salt.

38. The composition of claim 37, wherein the acid salt is mono-or-dibasic potassium or sodium phosphate, or sodium diacetate.

39. The composition of claim 17, wherein each part of the composition further comprises, independently, food grade inerts and surfactants.

40. A method of washing and reducing the microbial or viral count on foods, food surfaces or both comprising treating said foods, food surfaces or both with a dilute aqueous solution comprising about 0.1 to 400 grams per liter of a composition comprising in powder, non-aqueous liquid, gel, aerosol, or solid form:

(a) a source of a quaternary or protonizable nitrogen compound which is acceptable on foods, wherein the nitrogen compound is of the formula:

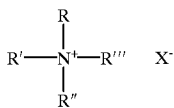

wherein X is an anion except a hydroperoxide anion;
R, R', R" and R'" are each independently H; a straight or branched, saturated or unsaturated, hydrocarbon group of 1–24 carbons; alkylamidoalkylene, alkylcarboxyalkylene, hydroxyalkylene, or alkoxyalkylene group having 1–8 carbon atoms, wherein the hydrocarbon, alkyl or alkylene chain may optionally be interrupted by one or more heteroatoms selected from the group consisting of nitrogen, sulfur, and phosphorus;

(b) an oxidant;

(c) a halide source comprising a metal halide salt, a halogen or a mixture thereof, wherein said halide or halogen comprises at least a bromine or iodine atom; and (d) optionally a food grade source of acidity;
wherein an aqueous solution thereof has a pH of about 9 or less and an ultraviolet absorption maximum at about 365 nm.

41. The method of claim 40, wherein the dilute aqueous solution comprises about 1 to 100 grams per liter of said composition.

42. The method of claim 40, wherein the food surface is a clean-in-place system, a clean-out-of-place system, a warewash machine, a sink, a food package, or a food transportation surface.

43. The method of claim 40, wherein the surface is an aseptic food package.

44. A method of reducing the microbial or viral count on animals or animal carcasses comprising treating said animals or animal carcasses with a dilute aqueous solution comprising about 0.1 to 400 grams per liter of a composition comprising in powder, non-aqueous liquid, gel, aerosol, or solid form:

(a) a source of a quaternary or protonizable nitrogen compound which is acceptable on foods, wherein the nitrogen compound is of the formula:

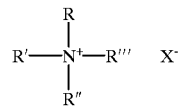

wherein X is an anion except a hydroperoxide anion;
R, R', R" and R'" are each independently H; a straight or branched, saturated or unsaturated, hydrocarbon group of 1–24 carbons; alkylamidoalkylene, alkylcarboxyalkylene, hydroxyalkylene, or alkoxyalkylene group having 1–8 carbon atoms, wherein the hydrocarbon, alkyl or alkylene chain may optionally be interrupted by one or more heteroatoms selected from the group consisting of nitrogen, sulfur, and phosphorus;

(b) an oxidant;

(c) a halide source comprising a metal halide salt, a halogen or a mixture thereof, wherein said halide or halogen comprises at least a bromine or iodine atom; and (d) optionally a food grade source of acidity;
wherein an aqueous solution thereof has a pH of about 9 or less and an ultraviolet absorption maximum at about 365 nm.

45. A method of reducing microbes and odors in animal feeds comprising treating said feeds with an effective amount of a composition comprising in powder, non-aqueous liquid, gel, aerosol, or solid form:

(a) a source of a quaternary or protonizable nitrogen compound which is acceptable on foods, wherein the nitrogen compound is of the formula:

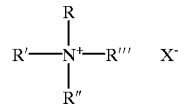

wherein X is an anion except a hydroperoxide anion;
R, R', R" and R'" are each independently H; a straight or branched, saturated or unsaturated, hydrocarbon group of 1–24 carbons; alkylamidoalkylene, alkylcarboxyalkylene, hydroxyalkylene, or alkoxyalkylene group having 1–8 carbon atoms, wherein the hydrocarbon, alkyl or alkylene chain may optionally be interrupted by one or more heteroatoms selected from the group consisting of nitrogen, sulfur, and phosphorus;

(b) an oxidant;

(c) a halide source comprising a metal halide salt, a halogen or a mixture thereof, wherein said halide or halogen comprises at least a bromine or iodine atom; and (d) optionally a food grade source of acidity;
wherein an aqueous solution thereof has a pH of about 9 or less and an ultraviolet absorption maximum at about 365 nm.

46. A method of washing and reducing the microbial or viral count on foods, food surfaces or both comprising:
(a) mixing a two part liquid concentrate comprising in one part:
  (i) about 0.1 to 80 wt % of a natural source of a quaternary or protonizable nitrogen compound which is acceptable on foods;
  (ii) about 0.1 to 75 wt % of an oxidant;
  (iii) about 0.1 to 75 wt % of a food grade acidity source; and
  (iv) the balance being water; and
in the second part:
  (v) about 0.1 to 80 wt % of a halide source comprising a metal halide salt, a halogen or a mixture thereof, wherein said halide or halogen comprises at least a bromine or iodine atom;
  (vi) the balance being water in water to provide a dilute aqueous solution of about 0.1 to 130,000 ppm of the total concentrate; and
(b) treating said foods, food surfaces or both with the resulting dilute aqueous solution.

47. The method of claim 46, wherein the food surface is a clean-in-place system, a clean-out-of-place system, a warewash machine, a sink, a food package, or a food transportation surface.

48. The method of claim 46, wherein the surface is an aseptic food package.

49. A method of reducing the microbial or viral count on animals or animal carcasses comprising treating said animals or animal carcasses according to claim 46.

50. A method of reducing microbial or viral count of water used in the production or transport of foods, beverages, and bottled water products comprising adding to said water a microbial or viral reducing effective amount of a composition comprising in one part:
(a) about 0.1 to 80 wt % of a natural source of a quaternary or protonizable nitrogen compound which is acceptable on foods;
(b) about 0.1 to 75 wt % of an oxidant;
(c) about 0.1 to 75 wt % of a food grade acidity source; and
(d) the balance being water; and
in the second part:
(e) about 0.1 to 80 wt % of a halide source comprising a metal halide salt, a halogen or a mixture thereof, wherein said halide or halogen comprises at least a bromine or iodine atom;
(f) the balance being water.

51. A method of reducing microbial or viral count of water used in rinsing foodware comprising adding to said water an effective amount of a composition comprising in one part:
(a) about 0.1 to 80 wt % of a natural source of a quaternary or protonizable nitrogen compound which is acceptable on foods;
(b) about 0.1 to 75 wt % of an oxidant;
(c) about 0.1 to 75 wt % of a food grade acidity source; and
(d) the balance being water; and
in the second part:
(e) about 0.1 to 80 wt % of a halide source comprising a metal halide salt, a halogen or a mixture thereof, wherein said halide or halogen comprises at least a bromine or iodine atom;
(f) the balance being water.

52. A method of reducing microbes and odors in animal feeds comprising treating said feeds with an effective amount of a composition comprising in one part:
(a) about 0.1 to 80 wt % of a natural source of a quaternary or protonizable nitrogen compound which is acceptable on foods;
(b) about 0.1 to 75 wt % of an oxidant;
(c) about 0.1 to 75 wt % of a food grade acidity source; and
(d) the balance being water; and
in the second part:
(e) about 0.1 to 80 wt % of a halide source comprising a metal halide salt, a halogen or a mixture thereof, wherein said halide or halogen comprises at least a bromine or iodine atom;
(f) the balance being water.

53. A method of reducing the microbial or viral count on foods, food surfaces or both comprising treating said foods, food surfaces or both with a dilute aqueous solution comprising about 0.1 to 400 grams per liter of an antimicrobial and antiviral composition comprising:
a complex of the formula

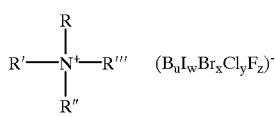

wherein R, R', R" and R'" are each independently H; a straight or branched, saturated or unsaturated, hydrocarbon group of 1–24 carbons; an alkylamidoalkylene, alkylcarboxyalkylene, hydroxyalkylene, or alkoxyalkylene group having 1–8 carbon atoms, wherein the hydrocarbon, alkyl or alkylene chain may optionally be interrupted by one or more heteroatoms selected from the group consisting of nitrogen, sulfur, and phosphorus;
B is a non-halogen anion, except hydroperoxy;
u is an integer from o to 1;
w is an integer from 1 to 8;
x and y are each independently integers from 0 to 8;
z is an integer from 0 to 1;
wherein the complex is not ammonium iodide; and
optionally a food grade source of acidity.

54. The method of claim 53, wherein x, y and z are 0.

55. A method of reducing the microbial or viral count on foods, food surfaces or both comprising treating said foods, food surfaces or both with a dilute aqueous solution comprising about 0.1 to 400 grams per liter of an antimicrobial and antiviral composition comprising:
a complex of the formula

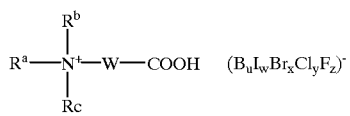

wherein $R^a$ is a linear or branched, saturated or unsaturated, hydrocarbon, hydroxyalkyl or alkoxyalkyl group having 1–22 carbon atoms; $R^b$ and RC are independently H or $CH_3$; W is a linear or branched alkylene, hydroxyalkylene or alkoxyalkylene group having 1–4 carbon atoms;

B is a non-halogen anion, except hydroperoxy;
u is an integer from 0 to 1;
w is an integer from 1 to 8;
x and y are each independently integers from 0 to 8;
z is an integer from 0 to 1; and
optionally a food grade source of acidity.

56. The method of claim 55, wherein x, y and z are 0.

57. A method reducing microbial or viral count of water used in the production or transport of foods, beverages, and bottled water products comprising adding to said water an antimicrobial and antiviral composition comprising:

a complex of the formula

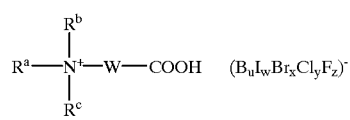

wherein $R^a$ is a linear or branched, saturated or unsaturated, hydrocarbon, hydroxyalkyl or alkoxyalkyl group having 1–22 carbon atoms; $R^b$ and $R^c$ are independently H or $CH_3$, W is a linear or branched alkylene, hydroxyalkylene or alkoxyalkylene group having 1–4 carbon atoms;
B is a non-halogen anion, except hydroperoxy;
u is an integer from 0 to 1;
w is an integer from 1 to 8;
x and y are each independently integers from 0 to 8;
z is an integer from 0 to 1; and
optionally a food grade source of acidity.

58. A method of reducing the microbial or viral count on foods, food surfaces or both comprising treating said food, food surfaces or both with a dilute aqueous solution comprising about 0.1 to 400 grams per liter of an antimicrobial and antiviral composition comprising:

a complex of the formula

wherein $R^d$ is a side chain of a natural amino acid moiety;
B is a non-halogen anion, except hydroperoxy;
u is an integer from 0 to 1;
w is an integer from 1 to 8;
x and y are each independently integers from 0 to 8;
z is an integer from 0 to 1; and
optionally a food grade source of acidity.

59. The method of claim 58, wherein x, y and z are 0.

60. A method reducing microbial or viral count of water used in the production or transport of foods, beverages, and bottled water products comprising adding to said water an antimicrobial and antiviral composition comprising:

a complex of the formula

wherein $R^d$ is a side chain of a natural amino acid moiety;
B is a non-halogen anion, except hydroperoxy;
u is an integer from 0 to 1;
w is an integer from 1 to 8;
x and y are each independently integers from 0 to 8;
z is an integer from 0 to 1; and
optionally a food grade source of acidity.

61. The method of claim 60, wherein x, y and z are 0.

62. A method of reducing the microbial or viral count on foods, food surfaces or both comprising treating said foods, food surfaces or both with a dilute aqueous solution comprising about 0.1 to 400 grams per liter of an antimicrobial and antiviral composition comprising:

a complex of the formula

wherein $[\text{polypeptide}]^+_{acidified}$ is a protonated simple or complex poly-amino acid or protein;
B is a non-halogen anion, except hydroperoxy;
u is an integer from 0 to 1;
w is an integer from 1 to 8;
x and y are each independently integers from 0 to 8;
z is an integer from 0 to 1;
t is an integer greater than 0; and
optionally a food grade source of acidity.

63. The method of claim 62, wherein x, y and z are 0.

64. A method reducing microbial or viral count of water used in the production or transport of foods, beverages, and bottled water products comprising adding to said water an antimicrobial and antiviral composition comprising:

a complex of the formula

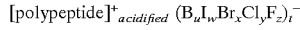

wherein $[\text{polypeptide}]^+_{acidified}$ is a protonated simple or complex poly-amino acid or protein;
B is a non-halogen anion, except hydroperoxy;
u is an integer from 0 to 1;
w is an integer from 1 to 8;
x and y are each independently integers from 0 to 8;
z is an integer from 0 to 1;
t is an integer greater than 0; and
optionally a food grade source of acidity.

65. The method of claim 64, wherein x, y and z are 0.

66. A process for preparing an antimicrobial or antiviral complex comprising reacting in a solvent-free medium a solid or powdered quaternary or protonizable nitrogen compound, which is acceptable on foods, with an oxidant and a halogen source in the presence of heat, moisture vapors or chemical hydrates.

* * * * *